(12) United States Patent
Feng et al.

(10) Patent No.: US 11,484,335 B2
(45) Date of Patent: Nov. 1, 2022

(54) SKIN SURFACE INDWELLING DEVICE FOR GUIDING PUNCTURES

(71) Applicant: Medtronic, Inc., Minneapolis, MN (US)

(72) Inventors: Yong Feng, Shanghai (CN); Yueqiang Xue, Shanghai (CN); Jian Song, Shanghai (CN); Kai Huang, Shanghai (CN); Chengrui Pan, Shanghai (CN); Xin Tang, Shanghai (CN); Jianming Zhou, Shanghai (CN); Zhenhua Yuan, Shanghai (CN); Jing Zhang, Shanghai (CN); Wei Hu, Shanghai (CN)

(73) Assignee: MEDTRONIC, INC., Minneapolis, MN (US)

( * ) Notice: Subject to any disclaimer, the term of this patent is extended or adjusted under 35 U.S.C. 154(b) by 262 days.

(21) Appl. No.: 16/076,348

(22) PCT Filed: Mar. 29, 2017

(86) PCT No.: PCT/CN2017/078525
§ 371 (c)(1),
(2) Date: Aug. 8, 2018

(87) PCT Pub. No.: WO2017/167192
PCT Pub. Date: Oct. 5, 2017

(65) Prior Publication Data
US 2019/0046233 A1    Feb. 14, 2019

(30) Foreign Application Priority Data
Mar. 29, 2016    (CN) .......................... 201610188985.4

(51) Int. Cl.
*A61B 17/34* (2006.01)
*A61M 5/158* (2006.01)
(Continued)

(52) U.S. Cl.
CPC ....... *A61B 17/3403* (2013.01); *A61M 1/3661* (2014.02); *A61M 5/158* (2013.01);
(Continued)

(58) Field of Classification Search
CPC ........ A61B 17/3403; A61B 2017/0089; A61B 2017/00951; A61M 5/158; A61M 5/3287;
(Continued)

(56) References Cited

U.S. PATENT DOCUMENTS

| 4,318,401 | A |   | 3/1982 | Zimmerman |
| 4,393,873 | A | * | 7/1983 | Nawash .............. A61J 15/0015 |
|           |   |   |        | 128/DIG. 26 |

(Continued)

FOREIGN PATENT DOCUMENTS

| CN | 1381279 A | 11/2002 |
| CN | 1671429 A | 9/2005 |

(Continued)

OTHER PUBLICATIONS

International Search Report for PCT/CN2017/078525 date of completion is May 22, 2017 (5 pages).

(Continued)

*Primary Examiner* — Kevin C Sirmons
*Assistant Examiner* — Leah J Swanson
(74) *Attorney, Agent, or Firm* — Shumaker & Sieffert, P.A.

(57) ABSTRACT

A skin surface indwelling device for guiding punctures includes: an indwelling tube (13) having an inside tunnel (P) substantially extending along the longitudinal direction of the indwelling tube (13), the tunnel (P) is used for guiding needle (N), the indwelling tube (13) has a proximal end positioned above the skin surface (S) and a distal end positioned under the skin surface (S) in indwelling state; a support (11) having a bottom surface on its bottom that (Continued)

directly or indirectly contacts with the skin surface (S), the support (11) supports and fixates the indwelling tube (13); and a sealing elements (141,142) configured to seal the tunnel (P). The skin surface indwelling device for guiding punctures can shorten the time of establishing a puncture tunnel in the buttonhole puncture method, and help to build the puncture tunnel. In addition, the skin surface indwelling device can also guide the puncture needle (N) when puncturing, and protect the immature puncture tunnel.

19 Claims, 20 Drawing Sheets

(51) Int. Cl.
*A61M 5/32* (2006.01)
*A61M 39/02* (2006.01)
*A61M 1/36* (2006.01)
*A61M 39/06* (2006.01)
*A61B 17/00* (2006.01)

(52) U.S. Cl.
CPC ...... *A61M 5/3287* (2013.01); *A61M 39/0247* (2013.01); *A61M 39/06* (2013.01); *A61B 2017/00889* (2013.01); *A61B 2017/00951* (2013.01); *A61M 2039/066* (2013.01); *A61M 2039/0646* (2013.01); *A61M 2205/0205* (2013.01); *A61M 2205/0216* (2013.01)

(58) Field of Classification Search
CPC .............. A61M 39/0247; A61M 39/06; A61M 2039/0646; A61M 2039/066; A61M 2205/0205; A61M 2205/0216; A61M 2005/1586; A61M 2039/0258; A61M 2039/027; A61M 2039/0273; A61M 2039/0276; A61M 2039/0279; A61M 2039/0282; A61M 2039/0285; A61M 25/02; A61M 25/04; A61M 2025/0206; A61M 2025/0213; A61M 2025/0233; A61M 2025/024; A61M 2025/0246; A61M 2025/0253; A61M 2025/026; A61M 2025/0266; A61M 2025/0273; A61M 2025/028; A61M 2025/0286; A61M 2025/0293

See application file for complete search history.

(56) References Cited

U.S. PATENT DOCUMENTS

| | | | | |
|---|---|---|---|---|
| 5,217,411 | A * | 6/1993 | Spector | A63G 11/00 472/101 |
| 5,217,441 | A * | 6/1993 | Shichman | A61B 17/3403 604/164.01 |
| 5,456,671 | A | 10/1995 | Bierman | |
| 5,728,103 | A * | 3/1998 | Picha | A61B 17/3423 604/174 |
| 6,572,624 | B2 * | 6/2003 | U | A61B 90/11 606/130 |
| 7,014,650 | B2 | 3/2006 | Ishihara et al. | |
| 9,039,615 | B2 * | 5/2015 | Flint | A61B 8/12 600/437 |
| 9,302,043 | B2 * | 4/2016 | Nelson | A61M 25/02 |
| 2004/0006316 | A1 * | 1/2004 | Patton | A61M 39/0247 604/244 |
| 2006/0155318 | A1 | 7/2006 | Shinzato et al. | |
| 2006/0217666 | A1 * | 9/2006 | Wenchell | A61B 17/3417 604/167.03 |
| 2008/0033344 | A1 * | 2/2008 | Mantell | A61M 39/0247 604/27 |
| 2011/0054403 | A1 * | 3/2011 | Tanabe | A61M 5/158 604/164.01 |
| 2011/0178467 | A1 | 7/2011 | Bierman et al. | |
| 2012/0179120 | A1 * | 7/2012 | Rohrscheib | A61M 39/0208 604/288.02 |
| 2013/0138080 | A1 * | 5/2013 | Andino | A61M 25/0015 604/508 |
| 2013/0289399 | A1 * | 10/2013 | Choi | A61B 17/1671 600/431 |
| 2017/0086813 | A1 * | 3/2017 | Hess | A61B 17/3403 |
| 2017/0095644 | A1 * | 4/2017 | Stephan | A61M 25/0111 |
| 2017/0135778 | A1 * | 5/2017 | Gill | A61M 25/0043 |
| 2019/0183524 | A1 * | 6/2019 | Badhwar | A61L 31/06 |

FOREIGN PATENT DOCUMENTS

| | | | |
|---|---|---|---|
| CN | 101378799 | A | 3/2009 |
| CN | 101460207 | A | 6/2009 |
| CN | 102186515 | A | 9/2011 |
| CN | 102886084 | | 1/2013 |
| CN | 102886084 | A | 1/2013 |
| CN | 205598348 | U | 9/2016 |
| CN | 205598349 | U | 9/2016 |
| CN | 205598350 | U | 9/2016 |
| CN | 101557845 | | 10/2019 |
| EP | 2859911 | A1 | 4/2015 |
| JP | 2015-213594 | A | 12/2015 |
| WO | WO-8701041 | A1 * | 2/1987 ........ A61M 39/0247 |

OTHER PUBLICATIONS

Office Action in Chinese App. No. 201610188985.4, dated Jun. 2, 2020.

Office Action in Chinese App. No. 201610188985.4, dated Jan. 6, 2020.

International Preliminary Report on Patentability from International Application No. PCT/CN2017/078525, dated Oct. 11, 2018, 7 pp.

* cited by examiner

SKIN SURFACE INDWELLING DEVICE FOR GUIDING PUNCTURES

CROSS-REFERENCE TO RELATED APPLICATIONS

This application is a National Stage Application of PCT/CN2017/078525 under 35USC § 371 (a), which claims benefit of and priority to Chinese Patent Application No. 201610188985.4 filed Mar. 29, 2016, the disclosures of each of the above-identified applications are hereby incorporated by reference in their entirety.

FIELD OF THE INVENTION

The invention relates to a medical device and in particular to a skin surface indwelling medical device.

BACKGROUND

Patients with renal disease need to be treated with hemodialysis at a frequency of 2 to 3 times a week. During hemodialysis, there is a need to place a dialysis needle or indwelling needle into human body. The dialysis needle or indwelling needle needs to enter into blood vessels through the skin, and thus it will bring much pain to the patients receiving hemodialysis treatment.

The current methods of dialysis needle or indwelling needle placement include area puncturing, rope ladder puncturing and buttonhole puncturing.

Among them, the area puncture method is a method that can puncture randomly in the area of available blood vessels. The advantages of the area puncture method are simple operation and low skill requirements for the operator. The disadvantage of the area puncture method is that there is a need to create a new puncturing point in each dialysis, thus a large area of damage on the skin surface and the vascular wall is caused, and thereby the risk of hemangioma, vascular stenosis, hematoma and other complications are greatly increased. In addition, permanent scars on the skin surface also severely decrease the quality of patients' life.

The rope ladder puncture method is a method of puncturing in the area of available blood vessels in accordance with the sequence of rope ladder. The advantage of the rope ladder puncture method is to limit the area of puncturing and reduce the number of puncturing points to protect the skin and blood vessels to a certain extent. The disadvantage of rope ladder puncture method is that this method is object to the range of blood vessels available for puncturing and this method has great limitation for patients with end-stage renal disease whose vascular conditions are not good.

Buttonhole puncture method is a long-term puncturing method from only two fixed puncturing points in the area of available blood vessels. The advantages of buttonhole puncture method are to greatly protect the skin and blood vessels, to reduce the complications caused by punctures, to relieve patients' pain by puncturing in the puncture tunnel which is formed by long-term and repeated puncturing, and to improve the appearance of the puncturing point at the same time. Based on this, the buttonhole puncture method has become a puncture method recommended in "*Guide of Chinese Hemodialysis Vascular Access Care*".

However, at present, buttonhole puncture method has not been widely adopted since its implementation is relatively more difficult. It is because that the puncture tunnel in the buttonhole puncture method is formed by repeated puncturing for 6~12 times, and repeated puncturing for 6~12 times requires experienced operators to ensure the consistence of the puncturing point, the puncturing angle and the puncturing depth every time when puncturing. Therefore, the buttonhole puncture method has high requirements for operators' operation skill threshold.

Therefore, a product or method is needed to be developed in order to reduce the difficulty of implementing buttonhole puncturing.

In the prior art, products for reducing the difficulty of implementing buttonhole puncturing and helping establish puncture tunnels mainly include two types:

One of them is the artificial port that is implanted into the blood vessels by surgery to ensure the consistency and accuracy of the puncture on the blood vessels. However, the artificial port usually has a complex structure, the implantation process leads to relatively large wounds on the skin and blood vessels of patients and the implanted artificial port also faces the risk that is not compatible with receptors, thereby leads to large subsequent treatment and maintenance costs.

The other type of products in the prior art is a placeholder. After pulling out the dialysis needle at the end of each dialysis treatment, the placeholder is inserted into the skin tunnel until the next puncture, so as to ensure that the wound of puncture tunnel shall not recover by itself at the intervals between two dialysis sessions. In addition, a smooth and flat connective tissue will be formed on the inner wall of the puncture tunnel along the placeholder, consequently to accelerate the formation of the tunnel. This type of products is described and introduced in NIPRO Corporation's patents titled "Hole-forming Pin for Inserting Indwelling Needle Insertion And Jig for Installing the Pin" (the publication number is CN1671429A, and the publication date is Sep. 21, 2005) and "Pin for Forming A Hole for Inserting An Indwelling Needle" (the publication number is CN1381279A, and the publication date is Nov. 27, 2002).

However, this products mentioned above can only hold the place for the puncture tunnel at intervals of hemodialysis, and because it is removed from the puncture tunnel in the process of puncturing, the immature tunnel cannot be protected while puncturing, the puncturing process cannot be guided, and thus formation of the original puncture tunnel may be damaged and the patient's treatment is further affected.

SUMMARY

The object of the invention is to provide a skin surface indwelling device for guiding punctures, which can help build the puncture tunnel like products in the prior art. Moreover, the skin surface indwelling device for guiding punctures mentioned in the invention can also protect the immature puncture tunnel while puncturing as well as guide the puncturing process at the same time, thereby greatly reduce the difficulty of implementation of the buttonhole puncture method and reduce the operation requirements of puncturing operators, and thus popularize the buttonhole puncture method.

Based on the above inventive object, the invention provides a skin surface indwelling device for guiding punctures, comprising:

an indwelling tube having an inside tunnel substantially extending along the longitudinal direction of the indwelling tube, wherein the tunnel is used for guiding a needle, the indwelling tube has a proximal end positioned above the skin surface and a distal end positioned under the skin surface in indwelling state;

a support having a bottom surface on its bottom that directly or indirectly contacts with the skin surface, wherein the support supports and fixates the indwelling tube; and sealing elements configured to seal the tunnel.

It should be noted that "proximal end" of the indwelling tube mentioned in the invention refers to the portion of the indwelling tube located above the skin surface in the indwelling state; similarly, "distal end" of the indwelling tube mentioned in the invention refers to the portion of the indwelling tube located below the skin surface in the indwelling occupying state.

The bottom of the support has a bottom surface that has a direct or indirect contact with the skin surface, wherein "direct contact" refers to that the bottom surface is directly attached to the skin surface, and "indirect contact" refers to that the bottom surface and skin surface are attached through a thin layer, such as the bottom surface are attached to the skin through an adhesive layer.

In the hemodialysis treatment sessions, the skin surface indwelling device for guiding punctures with the above structure helps the quick formation of the puncture tunnel, and can also protect the puncture tunnel and play a guiding role on the puncturing process of dialysis needle or puncture needle. When patients need hemodialysis, indwelling tube can enter into the subject through the skin surface along with puncture needle, or enter into the subject through the skin surface by itself. After completing a hemodialysis session and removing the indwelling needle, the distal end of the indwelling tube is still dwelt in the subject to play a role of placeholder, thus to form the puncture tunnel. In the next dialysis puncture, after the puncture needle enters into the subject through the tunnel of the indwelling tube, a dialysis treatment follows. In the puncturing process that the puncture needle enters into the subject, indwelling tube plays a guiding and protecting role. Since the position and inclination angle of the indwelling tube has been fixed by the support, no matter whether the operator of the dialysis puncture is the same person or whether the operator is of rich puncturing experience, every dialysis puncture can ensure an identical puncturing point, an identical puncturing angle and an identical puncturing depth, and thus reduce the implementation difficulty of the buttonhole puncture method.

In order to ensure adequate support force and strength, the support of the invention uses relatively hard materials comparing to the material of the indwelling tube, such as PC material. In order to minimize the damage of the subject as well, the indwelling tube of the invention uses relatively hard materials comparing to the support, such as polyurethane material. In addition, in order to ensure the biological compatibility, the indwelling tube of the invention should adopt a material with good biological compatibility.

It should be noted that skin surface indwelling device for guiding punctures of the invention is not only suitable for hemodialysis treatment, but also applicable to other treatments containing puncture operations (e.g., subcutaneous injection, subcutaneous minimally invasive surgery, biopsy, etc.), so the hemodialysis treatment does not serve as a limitation to the technical solution.

Preferably, on the skin surface indwelling device for guiding punctures of the invention, the extension length of the distal end is set in such a way that the bottom of the distal end is close to the vascular wall to be punctured but not in contact with the vascular wall to be punctured.

By adopting the above structure, the distal end of the indwelling tube is not in contact with the vascular wall and thus does damage the vascular wall, thereby a better implementation effect of the present solution can be achieved.

Of course, in other embodiments, the distal end of the indwelling catheter may also be configured to be in contact with the vascular wall.

Preferably, on the skin surface indwelling device for guiding punctures of the invention, the diameter of the tunnel is slightly larger than the outer diameter of the needle.

By adopting the above structure, the puncture needle can receive relatively small frictional resistance when the puncture needle passes through the tunnel of the indwelling tube, thereby a better implementation effect of the present solution can be achieved.

Further, in the skin surface indwelling device for guiding punctures of the invention, the angle between the bottom surface of the support and the axis of the indwelling tube is 20 to 40 degrees.

In the technical scheme, the puncturing angle of the puncture needle is determined by the angle between the bottom surface of the support and the axis of the indwelling tube. Although for different operators, the puncturing angle may be different, but it is generally in the range of 20-40 degrees. In addition, as for the same patient who receives dialysis, the puncturing angle of each puncturing operation is expected to be the same. Therefore, once the first puncture has taken, the angle should be a determined constant angle value.

Preferably, in the skin surface indwelling device for guiding punctures of the invention, the inner surface and/or the outer surface of the indwelling tube or the inner surface and/or the outer surface of the distal end of the indwelling tube is coated with an antibacterial coating.

By adopting the above structure, the technical solution is given a better antibacterial and bacteria preventing effect, thereby the risk of infection during subcutaneous implantation is reduced. The antibacterial coating may be a silver ion coating or a sulfadiazine coating, or other antibacterial coatings known by a skilled person in the art.

Preferably, in the skin surface indwelling device for guiding punctures of the invention, the bottom surface of the support is provided with a plurality of protrusions that protrudes from the bottom surface.

The bottom surface is provided with a plurality of protrusions, which improves the effect of connection on one hand, and also produces a certain gap between the bottom surface and the skin surface on the other hand, thereby the air permeability of the skin surface is improved and the risk of cutaneous anaphylaxis is reduced.

Further, the skin surface indwelling device for guiding punctures of the invention further comprises a bacteria-preventing waterproof air-permeable membrane which covers a portion of the skin surface indwelling device above the skin surface.

Since the skin surface indwelling device for guiding punctures of the invention is indwelt on the skin surface, in order to further improve antibacterial and bacteria preventing effect, a bacteria-preventing waterproof air-permeable membrane covering it can be used in the indwelling period. In addition, a bacteria-preventing waterproof air-permeable membrane further plays a role of attaching the skin surface indwelling device to the skin surface.

Further, in the skin surface indwelling device for guiding punctures of the invention, the outer contour of the support is hemisphere-shaped, arch-shaped or mouse-shaped.

To configure the outer contour of the support to the above shapes helps to hold the support during operation. Of course, other shapes of the support known by the skilled person in the art that can achieve the technical effects of the present solution can also be used.

Further, in the skin surface indwelling device for guiding punctures of the invention, the support has recesses for being held with fingers.

It should be noted that the invention could include one or more of the preferable or additional technical features mentioned above in the different embodiments, and the one or more features can be combined freely.

Based on the skin surface indwelling device for guiding punctures of the invention, the invention also provides a method of using a skin surface indwelling device for guiding punctures, comprising:

(1) guiding the indwelling tube into the subject through the skin surface in the first session;

(2) after the first session, indwelling the skin surface indwelling device on the skin surface so as to indwell the distal end of the indwelling tube in the subject to hold a place, thereby to help form a puncture tunnel;

(3) before the subsequent session, inserting a needle into the subject through the tunnel of the indwelling tube so as to carry out the subsequent session;

repeating Step (3) until the whole treatment is finished.

The above sessions may be either hemodialysis or other sessions such as subcutaneous injection.

In addition, at the end of each session, a layer of bacteria-preventing waterproof air-permeable membrane can be covered on the skin surface indwelling device indwelt on the skin surface, and before the subsequent session, first removing bacteria-preventing waterproof air-permeable membrane, and then inserting the puncture needle into the subject through the tunnel of the indwelling tube.

As the first embodiment of the invention, in the skin surface indwelling device for guiding punctures of the invention, the support has a removable fixed connection with the indwelling tube, and after connecting the support and the proximal end of the indwelling tube, the support keeps the angle between the bottom surface of the support and the axis of the indwelling tube unchanged.

In this embodiment, the support has a removable fixed connection with the indwelling tube, which enables the operator to select a puncturing angle according to his or her operating habits or requirements of the patients in the operation process. And then connecting the support and the proximal end of the indwelling tube after the distal end of the indwelling tube enters into the distal end of the subject so as to fix the angle between the bottom surface of the support and the axis of the indwelling tube and keep it unchanged.

The advantages of this embodiment are that since the angle between the axis of the indwelling tube and the bottom surface of the support is adjustable, the skin surface indwelling device of the same specification can be suitable for different operators and patients.

Further, in this embodiment, the indwelling tube includes a tube body and a spherical head radially protrudes from the tube body, and the spherical head is provided on the proximal end of the indwelling tube; wherein the support is correspondingly configured to have a first cavity which suitably receives part of the tube body and a second cavity which suitably receives the spherical head.

The setting of the above structure makes the angle of the indwelling tube entering into the subject variable, so as to make the adjustment of the angle between the bottom surface of the support and the axis of the indwelling tube more convenient. Of course, the invention can also adopt other structures which fulfill the adjustment of the angle between the bottom surface of the support and the axis of the indwelling tube. In addition, in this embodiment, the length of the indwelling tube entering into the subject, i.e. the extension length of the distal end of the indwelling tube, will be restricted by the connection with the spherical head the support, that is to say, for the same skin surface indwelling device, the extension length of the distal end of the indwelling tube is constant.

Alternatively, in the above embodiment, the spherical head and the second cavity are connected under an interference fit.

Alternatively, in the above embodiment, the outer surface of the spherical head and/or the inner surface of the second cavity has raised patterns which increase the friction force between the outer surface of the spherical head and the inner surface of the second cavity.

The raised patterns mentioned above could be spiral patterns, tooth-shaped patterns or other raised patterns which increase the friction force between the outer surface of the spherical head and the inner surface of the second cavity.

Further, in the above embodiment, the support has a U-shaped opening to allow the spherical head to enter into the second cavity.

Yet further, in the above embodiment, the U-shaped opening is an elastic U-shaped opening with an opening diameter slightly smaller than that of the outer diameter of the spherical head.

By adopting the above structure, the spherical head can easily slide into the second cavity of the support, and thereby quickly is connected with the support and the proximal end of the indwelling tube.

Further, in the above embodiment, the sealing elements includes at least one of a first sealing element and a second sealing element, wherein the first sealing element is positioned to correspond to the distal end of the indwelling tube and the second sealing element is positioned to correspond to the proximal end of the indwelling tube.

Preferably, the sealing element includes the first sealing element and the second sealing element respectively positioned at the distal end and the proximal end in order to further improve the sealing effect; wherein the first sealing element at the distal end can prevent blood or body fluids of the subject from entering into the indwelling tube, while the second sealing element at the proximal end can prevent external contaminants from entering into the indwelling tube.

As a preferably embodiment, the first sealing element and/or the second sealing element is positioned in the tunnel, and the first sealing element and/or the second sealing element is a sealing membrane or a sealing plug.

A sealing membrane or a sealing plug can achieve a relatively good effect of sealing, which can not only achieve the sealing of liquid (e.g. preventing the blood or body fluids of the subject from entering into the indwelling tube) but also achieve the sealing of gas, and thus it can prevent bacteria and microorganisms from entering into the indwelling tube along with air.

More preferably, the sealing membrane or sealing plug is a self-sealing membrane or a self-sealing plug.

The self-sealing membrane or the self-sealing plug can be made of silica gel, butyl rubber or other self-sealing materials.

By adopting the self-sealing membrane or the self-sealing plug, the sealing element is used repeatedly other than is disposed or replaced after a single use, thus saving the material cost.

As another preferably embodiment, the first sealing element is disposed at the bottom of the distal end of the indwelling tube and is formed to be a part of the indwelling tube; wherein the first sealing element is configured to allow the needle to enter into the subcutaneous tissue via the first sealing element while not to allow body fluid to enter into the tunnel from the subcutaneous tissue via the first sealing element.

That is to say, the first sealing element allows the puncture needle to enter into the subject through it, but does not allow the blood or body fluid from the subject in the opposite direction to enter into the tunnel of the indwelling tube.

The first sealing element can be a duckbill valve or nipple-shaped valve. The first sealing element can be a duckbill valve or a nipple-shaped valve. The so-called "duckbill valve" is a flat mouth valve with an end having a line-shaped opening known in the art. The so-called "nipple-shaped valve" is a kind of valve structure similar to the nipple which has a hole at its end, and the hole can be a circular hole, a Y-shaped hole, a cross hole, a star-shaped hole or the like.

Further, in the above embodiment, is the distal end has a wedge-shaped portion or an arc-shaped portion with an outer diameter tapering toward the bottom of the distal end.

This structure can reduce the resistance of the indwelling tube in the process of entering into the subject, thus making the indwelling tube easily enter into the subject.

Further, in the above embodiment, the material of the indwelling tube is selected from polyurethane, PEBAX (block polyether acidamide resin), LDPE (low-density polyethylene) or other materials with stable biological compatibility.

The indwelling tube made of the above material is relatively hard, so that the indwelling tube has a better formability, and thereby the indwelling tube can play a better role of support, placeholder and protection.

Further, the wall thickness of the indwelling tube is 0.1-1 mm.

Further, in the above embodiment, the bottom surface of the support is provided with an adhesive layer which has a first face adhered to the bottom surface and a second face adhered to the skin surface.

The adhesive layer makes the support be attached to the skin surface more stably, so as to provide the indwelling tube with a more stable support.

Furthermore, the adhesive layer is a U-shaped adhesive sticker with release paper.

The above adhesive layer can achieve quick attachment between the support and the skin surface. When attaching the support, a U-shaped release paper can be uncovered from either end of it, and then be removed from the gum clockwise or counterclockwise.

Based on the skin surface indwelling device for guiding punctures in the first embodiment above, the invention also provides a method of use of the device, comprising:

(1) at the beginning of the first session, inserting a needle through the tunnel of the indwelling tube, and then puncturing the needle together with the indwelling tube into the subject through the skin surface, and then connecting the support to the proximal end of the indwelling tube to fix the support in order to keep the angle between the bottom surface of the support and the axis of the indwelling tube unchanged;

(2) after the first session, removing the needle from the subject, and then indwelling the skin surface indwelling device on the skin surface so as to indwell the distal end of the indwelling tube in the subject to hold a place, thereby helping to form a puncture tunnel;

(3) before the subsequent session, inserting the needle into the subject through the tunnel of the indwelling tube to carry out the subsequent session; said indwelling tube is the indwelling tube of the used skin surface indwelling device indwelt on the skin surface after the last session or the indwelling tube of a new skin surface indwelling device indwelt on the skin surface after removing the used skin surface indwelling device at the beginning of the subsequent session;

repeating Step (3) until the whole treatment is finished.

The above sessions may be either hemodialysis or other sessions such as subcutaneous injection.

Preferably, at the end of each session, a layer of bacteria-preventing waterproof air-permeable membrane can be covered on the skin surface indwelling device indwelt on the skin surface, and before the subsequent session, first removing bacteria-preventing waterproof air-permeable membrane, and then inserting the needle or puncture needle into the subject through the tunnel of the indwelling tube.

It should be noted that, in the first embodiment, when the first sealing element and the second sealing element are both self-sealing elements, the skin surface indwelling device for guiding punctures can be indwelt on the skin surface for several days or for several sessions, for example for 3-5 days or for 3-5 sessions. Of course, the appropriate time or the appropriate times of the skin surface indwelling device indwelt on the skin surface can also be reduced or increased appropriately according to the biological compatibility of the skin surface indwelling device.

In addition, you can also choose to replace a new skin surface indwelling device every session. Of course, before the replacement of the new skin surface indwelling device, it is necessary to remove the used skin surface indwelling device.

As the second embodiment of the invention, the proximal end of the indwelling tube is fixed in the support, an opening is provided on the support for communicating with the tunnel of the indwelling tube.

Different from the first embodiment, in the second embodiment, the proximal end of the indwelling tube is connected with the support solidly instead of detachably, so that the angle between the axis of the same indwelling tube and the bottom surface of the support is fixed from the beginning, and is not adjustable. Therefore, in order to meet the needs of different operators or patients, different specifications of skin surface indwelling devices can be provided, namely, the angle between the bottom surface of the support and the axis of the indwelling tube of the skin surface indwelling devices of different specifications may vary, and even the distal ends of the indwelling tube of different specifications may have different lengths.

Although for the same skin surface indwelling device, the angle between the bottom surface of the support and the axis of the indwelling tube is no longer adjustable, compared with the first embodiment mentioned above, the structure of the skin surface indwelling device in this embodiment is simpler, and therefore the method of use is simpler.

In the second embodiment, the proximal end of the indwelling tube can have a solid connection with the support by means of attachment. Of course, the solid connection between the proximal end of the indwelling tube and the support can also be achieved by the other fixation ways known in the art.

Preferably, in the second embodiment, the opening is wedge-shaped with an inwardly decreasing diameter.

The wedge-shaped opening can play a guiding role for the puncture needle that is about to enter into the tunnel.

Preferably, in the second embodiment, the support includes a supporting portion and a cover separated with the supporting portion, and a hole of the supporting portion together with a hole of the cover forms the opening.

The support adopts a separating arrangement, which is convenient for the proximal end of the indwelling tube to be fixedly arranged in the support.

Further, in the second embodiment, the indwelling tube is a blind tube with the bottom of the distal end closed, and the sealing elements include the closed bottom of the distal end which is configured to be able to be pierced by the needle.

Preferably, in the second embodiment, the closed bottom of the distal end is wedge-shaped or arc-shaped.

The structure can reduce the resistance of the indwelling tube body in the process of entering into the subject, thereby making the indwelling tube easily enter into the subject.

Preferably, in the second embodiment, the wall thickness and/or hardness of the closed bottom of the distal end is smaller than those of the other parts of the indwelling tube.

The wall thickness and/or hardness of the other parts of the indwelling tube is relatively large, in order to ensure adequate strength and hardness of the tube body, thereby to provide better support force and strength as a placeholder during the formation of the puncture tunnel, and at the same time to provide better protection for the tissue of the subject in the puncturing process. The wall thickness and/or hardness of the closed bottom of the distal end is relatively small, which makes the puncture needle easily puncture it in the puncturing process.

Preferably, in the second embodiment, the sealing element further comprises a sealing membrane or a sealing plug which is disposed at the proximal end of the indwelling tube or the opening of the support.

Disposing the sealing membrane or the sealing plug at the proximal end of the indwelling tube or the opening of the support can further improve the sealing effect of the sealing element, so as to prevent the external contaminants from entering into the indwelling tube. A sealing membrane or a sealing plug can achieve a good sealing effect, which can not only achieve the sealing of liquid (for example, to prevent blood or body fluids of the subject from entering into the indwelling tube), but also can achieve even the sealing of gas, so it can prevent bacteria and microorganisms from entering into the indwelling tube together with air. The sealing membrane or the sealing plug can be made of silica gel, PTEE, or other suitable polymer materials.

More preferably, the support includes a supporting portion and a cover separated with the supporting portion, the hole of the supporting portion and that of the cover form the opening together, and the sealing element further comprises a sealing membrane fixed between the supporting portion and the cover.

It is a relative convenient installation method to arrange the sealing membrane between the supporting portion and the cover and fix it on the supporting portion by the cover.

Preferably, the sealing membrane or sealing plug is a self-sealing membrane or a self-sealing plug.

Based on the skin surface indwelling device for guiding punctures in the second embodiment above, the invention also provides a method of use of the device, comprising:

(1) at the beginning of the first session, inserting the needle into the subject to carry out the first session;

(2) after the first session, removing the needle from the subject, then gradually inserting the indwelling tube into the subject through the skin surface along a puncture path of the needle until the bottom surface of the support and the skin surface are in contact with each other; and then indwelling the skin surface indwelling device on the skin surface so as to indwell the distal end of the indwelling tube in the subject to hold a place, thereby helping to form a puncture tunnel;

(3) before the subsequent session, inserting the needle into the subject through the tunnel of the indwelling tube to carry out the subsequent session;

(4) after the subsequent session, removing the skin surface indwelling device and the needle from the subject, and then inserting the distal end of the indwelling tube of a new skin surface indwelling device into the subject along the puncture tunnel to indwell the new skin surface indwelling device on the skin surface;

repeating Steps (3) and (4) until the whole treatment is finished.

The above sessions may be either hemodialysis or other sessions such as subcutaneous injection.

In addition, at the end of each session, a layer of bacteria-preventing waterproof air-permeable membrane can be covered on the skin surface indwelling device indwelt on the skin surface, and before the subsequent session, first removing bacteria-preventing waterproof air-permeable membrane, and then inserting the puncture needle into the subject through the tunnel of the indwelling tube.

It can be seen from the description above that the use of the skin surface indwelling device for guiding punctures in the second embodiment is disposable, that is to say, it only allows the puncture needle to puncture once, and once the bottom of the distal end of the blind tube is pierced, it is replaced with a new skin surface indwelling device after the session in order to ensure the sealing effect.

However, if the selected material can achieve self-sealing of the blind tube, the skin surface indwelling device can also be reused.

As the third embodiment of the invention, in the skin surface indwelling device for guiding punctures, the proximal end of the indwelling tube is fixed in the support which has an opening, and the opening and the tunnel of the indwelling tube are jointly communicated with each other; the sealing element includes a sealing pin which can be inserted into the indwelling tube via the opening. The length of the sealing pin is set in such a way that a first end of the sealing pin extends out of the bottom of the distal end of the indwelling tube when the sealing pin is inserted into the indwelling tube to seal the tunnel.

Different from the above two embodiments, the sealing element in this embodiment is configured as a sealing pin which is coaxially disposed in the indwelling tube. The sealing effect of the sealing pin in the tunnel of the indwelling tube is achieved through the tolerance of fit between the outer surface of the sealing pin and the inner surface of the indwelling tube. This sealing solution usually achieves sealing of liquid (for example, preventing blood or body fluids of the subject from entering into the indwelling tube). In addition, since the first end of the sealing pin extends out of the bottom of the distal end of the indwelling tube, the portion of the sealing pin which extends out of the bottom of the distal end of the indwelling tube also plays the role of a placeholder after being dwelt on the skin surface. In addition, the sealing pin positioned in the indwelling tube can also play the role of enhancing the wall strength of the indwelling tube. That is, the sealing pin can also play the role of supporting the indwelling tube in this embodiment.

In the third embodiment, the skin surface indwelling device can still have the technical feature mentioned above that "the bottom of the distal end of the indwelling tube is close to the punctured vascular wall instead of being in contact with the punctured vascular wall". Since the first end of the sealing pin extends out of the bottom of the distal end of the indwelling tube, the first end of the sealing pin is closer to the vascular wall comparing to the bottom of the distal end of the indwelling tube. At this time, in order not to increase the pressure of the vascular wall, it is preferable to position the first end of the sealing pin close to the punctured vascular wall instead of being in contact with the punctured vascular wall as well. This setting mode will not make the vascular wall being pressed, and thus will not cause a damage to the vascular wall.

Of course, in other embodiments, the first end of the sealing pin can also be configured to be in contact with the vascular wall.

Preferably, in the third embodiment, the opening is wedge-shaped with an inwardly decreasing diameter.

The wedge-shaped opening may play a guiding role for the puncture needle that is about to enter into the tunnel.

Further, in the third embodiment, the sealing pin further comprises a connecting element connected with a second end of the sealing pin, and the connecting element is configured to be quickly detachably connected to the support.

Further, the connecting element is provided with first claws, and accordingly, the support is provided with matching grooves which match with the first claws, wherein the first claws and the matching grooves are connected to achieve the quickly detachable connection between the connecting element and the support.

Further, the connecting element includes a U-shaped beam fixedly connected with the second end of the sealing pin, wherein the first claws are disposed at the ends of the two arms of the U-shaped beam, and wherein the two arms of the U-shaped beam and the first claws disposed at the ends of the two arms of the U-shaped beam can get closer to each other under pressure and recover after releasing the pressure.

Further, in the third embodiment, the skin surface indwelling device for guiding punctures includes an auxiliary element, wherein the first end of the auxiliary element is provided with second claws which matches with the matching grooves, and the second claws and the matching grooves are connected to achieve the quickly detachable connection between the auxiliary element and the support; the second end of the auxiliary element is provided with a connecting portion for being connected with the needle; the auxiliary element is also provided with a slot for receiving the needle.

The auxiliary element mentioned above is used for removing the skin surface indwelling device of the third embodiment above. Before the puncture needle entering into the subject through the indwelling tube, at first, connecting the auxiliary element with the puncture needle through the connecting element at its second end, then puncturing the puncture needle into the subject through the indwelling tube; after the puncture needle is punctured into the subject, the first end of the auxiliary element achieves the quickly detachable connection with the support through a connection between the second claws and the matching grooves. After the session, when the skin surface indwelling device needs to be removed, due to the connection between the auxiliary element and the puncture needle and the support, once a force is applied on the puncture needle, the puncture needle can be removed from the subject together with the skin surface indwelling device.

Further, the connecting element includes radially inward a lug boss for matching with a corresponding groove on the needle.

As another embodiment of the quickly detachable connection with the connecting element and the support, the connecting element includes a U-shaped beam fixedly connected with the second end of the sealing pin, the ends of the two arms of the U-shaped beam are provided with wedge-shaped guide posts, accordingly, the support is provided with matching holes which match with the wedge-shaped guide posts; the connecting element further comprises an O-ring fixedly disposed on the sealing pin at the position close to the second end of the sealing pin, when the sealing pin is inserted into the indwelling tube to seal the tunnel, the O-ring is disposed between the sealing pin and the support to increase the friction force between the sealing pin and the support.

Preferably, in the third embodiment, the support is further provided with process holes which are used for forming the matching grooves or the matching holes by injection molding.

Further, in the third embodiment, sealing pin is solid or hollow, wherein the hollow sealing pin at least has a closed first end.

If the sealing pin is configured as a solid structure, it can provide a better support for the wall of the indwelling tube relative to the hollow structure. However, the sealing pin with the hollow structure will save more materials, thereby reducing the cost of products.

Preferably, in the third embodiment, the first end of the sealing pin is wedge-shaped or arc-shaped.

This structure can reduce the resistance of the indwelling tube in the process of entering into the subject, thereby making the indwelling tube and the first end of sealing pin easily enter into the subject.

As one mode of the third embodiment, the outer diameter of the sealing pin is configured that the sealing pin is consistently in close fit with the indwelling tube in the axial direction of the sealing pin and indwelling tube.

In this above structure, since the sealing pin is always in close fit with the indwelling tube, the technical solution has a relatively good sealing effect, which can ensure that no blood or body fluids will enter into the space between the indwelling tube and the sealing pin after the indwelling tube and sealing pin enter into the subcutaneous tissue. In addition, since the sealing pin is always in close fit with the indwelling tube, the sealing pin can also provide a stronger support for the wall of the indwelling tube.

As another realizing way of the third embodiment, the sealing pin includes at least a first portion and a second portion adjoining to the first portion in the axial direction thereof; the second portion is disposed at or close to the first end of the sealing pin, wherein the outer diameter of the first portion is slightly smaller than that of the second portion, and the outer diameter of the first portion is slightly smaller than the inner diameter of indwelling tube so that a clearance is formed between the first portion and the indwelling tube, while the second portion is in a close fit with the indwelling tube.

In the above structure, the sealing pin is always in close fit with the indwelling tube only at its first end. The outer diameter of the other parts of the sealing pin is slightly smaller than the inner diameter of the indwelling tube (i.e. the diameter of the "tunnel" mentioned above) in order to reduce the frictional resistance when the sealing pin enters into or exits the indwelling tube, and thereby makes it easier for the sealing pin to enter into or exit the indwelling tube. Preferably, in the third embodiment above, the outer surface of the sealing pin is coated with an antibacterial coating.

The antibacterial coating may be a silver ion coating or a sulfadiazine coating, or other antibacterial coatings known by a skilled person in the art.

Based on the skin surface indwelling device for guiding punctures in the third embodiment above, the invention also provides a method of use of the device, comprising:

(1) at the beginning of the first session, inserting the needle into the subject to carry out the first session;

(2) after the first session, removing the needle from the subject, then gradually inserting the indwelling tube together with the sealing pin into the subject through the skin surface along a puncture path of the needle until the bottom surface of the support and the skin surface are in contact with each other; and then indwelling the skin surface indwelling device on the skin surface so as to indwell the distal end of the indwelling tube and the sealing pin in the subject to hold a place, thereby helping to form a puncture tunnel;

(3) before the subsequent session, removing the sealing pin from the indwelling tube, and then inserting the needle into the subject through the tunnel of the indwelling tube to carry out the subsequent session;

(4) after the subsequent session, removing the skin surface indwelling device and the needle from the subject, and then inserting the distal end of the indwelling tube together with the sealing pin of a new skin surface indwelling device into the subject along the puncture tunnel to indwell the new skin surface indwelling device on the skin surface;

repeating Steps (3) and (4) until the whole treatment is finished.

The above sessions may be either hemodialysis or other sessions such as subcutaneous injection.

In addition, at the end of each session, a layer of bacteria-preventing waterproof air-permeable membrane can be covered on the skin surface indwelling device on the skin surface, and before the subsequent session, first removing bacteria-preventing waterproof air-permeable membrane and pulling the sealing pin from the indwelling tube, then inserting the puncture needle into the subject through the tunnel of the indwelling tube.

It can be seen from the description above that the use of the skin surface indwelling device for guiding punctures in the third embodiment is disposable, that is to say, it is better not to be used repeatedly. It is because that the first end of the sealing pin is in contact with the subcutaneous tissue of the subject in the indwelling state, while the sealing pin needs to be removed in the subsequent session, which makes the sealing pin polluted by the external contaminants. Therefore, in order to ensure that the device is sterile, it is recommended that a new skin surface indwelling device is replaced in each session.

Further, when the skin surface indwelling device for guiding punctures in the third embodiment includes the auxiliary element, Step (3) further comprises the following processes: before the subsequent session, removing the sealing pin from the indwelling tube, then inserting the needle connected with an auxiliary element into the subject through the tunnel of the indwelling tube, and then connecting the auxiliary element to the support when the needle reaches a certain subcutaneous position, so as to carry out the subsequent session; Step (4) further comprises the following processes: after the subsequent session, applying a pulling force on the needle to pull the needle together with the skin surface indwelling device out of the subject, and then inserting the distal end of the indwelling tube together with the sealing pin of a new skin surface indwelling device into the subject along the puncture tunnel to indwell the new skin surface indwelling device on the skin surface.

As the fourth embodiment of the invention, in the skin surface indwelling device for guiding punctures of the invention, the proximal end of the indwelling tube is fixed in the support which has an opening, and the opening and the tunnel of the indwelling tube are jointly communicated with each other; the sealing element includes a sealing pin including a sealing pin which can be inserted into the indwelling tube via the opening. The length of the sealing pin is set in such a way that the first end of the sealing pin extends out of the bottom of the distal end of the indwelling tube when the sealing pin is inserted into the indwelling tube to seal the tunnel. In addition, the support comprises a ridge portion and wings extending out from the ridge portion. The bottom surfaces of the wings form or partially form the bottom surface of the support.

It is the same as the previous three embodiments that the sealing element in the embodiment is also configured as a sealing pin, and the sealing pin of the sealing pin is coaxially disposed in the indwelling tube. In addition, the first end of the sealing pin extends out of the bottom of the distal end of the indwelling tube. The sealing effect of the sealing pin in the tunnel of the indwelling tube is achieved through the tolerance of fit between the outer surface of the sealing pin and the inner surface of the indwelling tube. This sealing solution usually achieves the sealing of liquid, (for example, preventing blood or body fluids of the subject from entering into the indwelling tube). In addition, since the first end of the sealing pin extends out of the bottom of the distal end of the indwelling tube, the portion of the sealing pin which extends out of the bottom of the distal end of the indwelling tube also plays the role of a placeholder after being dwelt on the skin surface. In addition, the sealing pin positioned in the indwelling tube can also play the role of enhancing the wall strength of the indwelling tube. That is, the sealing pin can also play the role of supporting the indwelling tube in this embodiment.

In the fourth embodiment, the skin surface indwelling device can still have the technical feature of "the extension length of the distal end is set in such a way that the bottom of the distal end is close to the vascular wall to be punctured instead of being in contact with the vascular wall to be punctured" as mentioned above. However, the first end of the sealing pin extends out of the bottom of the distal end of the indwelling tube, so that the first end of the sealing pin is closer to the vascular wall relative to the bottom of the distal end of the indwelling tube. Thus, it is preferable to set the first end of the sealing pin to be close to the vascular wall to be punctured but not in contact with the vascular wall to be punctured, in order to not increase the pressure on the vascular wall. Such structure will not impose extra pressure on the vascular wall, and therefore will not cause trauma to the vascular wall.

Alternatively, in other embodiments, it is possible to configure that the first end of the sealing pin contacts the vascular wall.

Different from the above three embodiments, in the fourth embodiment, the support comprises a ridge portion and wings extending out from the ridge portion. In this way, a better supporting force is provided by the support. Besides, the support with the wings can be conveniently held by operators during operations.

Further, in the fourth embodiment, the wings or the support is made of silica gel, rubber or polypropylene, or other materials with stable biological compatibility.

The above-mentioned materials are soft so that the wings can be folded or bent at a certain angle when held, and thus convenient for the operations of the operators.

Further, in the fourth embodiment, a first end of the ridge portion has a groove which is served as a point where a force is applied to take the sealing pin out of the indwelling tube; and wherein the first end of the ridge portion is the end relatively close to the opening of the support.

The groove can be used for taking the sealing pin out of the indwelling tube in an easier way.

Further, in the fourth embodiment, the sealing pin is solid or hollow, wherein the hollow pin at least has a closed first end.

The solid sealing pin can provide a stronger support force for the tube wall of the indwelling tube in view of the hollow sealing pin. However, the hollow sealing pin saves more materials, and thus reducing the product cost.

Further, in the fourth embodiment, the first end of the sealing pin is wedge-shaped or arc-shaped.

Such structure can reduce the resistance to the sealing pin together with the indwelling tube during the process of entering into the subject, which make the indwelling tube and the first end of the sealing pin enter into the subject more easily.

As an example of the fourth embodiment, the outer diameter of the sealing pin is configured that the sealing pin is consistently in close fit with the indwelling tube in the axial direction of the sealing pin and indwelling tube.

A better sealing effect that blood or body fluid would not enter into the clearance between the indwelling tube and the sealing pin after the indwelling tube and the sealing pin entering into the subcutaneous tissue can be achieved by means of the sealing pin consistently in close fit with the indwelling tube. In addition, the sealing pin can also provide a stronger support force for the tube wall of the indwelling tube, due to the structure of the pin being consistently in close fit with the indwelling tube.

As another example of the fourth embodiment, the sealing pin includes at least a first portion and a second portion adjoining to the first portion in the axial direction thereof; the second portion is disposed at or close to the first end of the sealing pin; wherein the outer diameter of the first portion is slightly smaller than the outer diameter of the second portion, and the outer diameter of the first portion is slightly smaller than the inner diameter of indwelling tube, so that a clearance is formed between the first portion and the indwelling tube, while the second portion is in a close fit with the indwelling tube.

In such configuration, the sealing pin is in close fit with the indwelling tube only at the first end thereof to ensure the sealing effect, while the outer diameter of the rest part of the sealing pin is slightly smaller than the inner diameter (namely the diameter of the "tunnel" mentioned above) of the indwelling tube to reduce the friction force generated by the process of the sealing pin getting in and out of the indwelling tube, and thus making the sealing pin get in and out of the indwelling tube more easily.

Preferably, in the above fourth embodiment, the outer surface of the sealing pin is coated with an antibacterial coating.

The anti-bacterial coating can be sliver ion coating or sulfadiazine coating or other antibacterial coatings known by those skilled in the art.

Further, in the fourth embodiment, the sealing pin further includes a stop lug boss connected with the second end of the sealing pin, and the stop lug boss radially protrudes from the sealing pin.

The stop lug boss is used to prevent the sealing pin from further extending into the indwelling tube in the axial direction of the indwelling tube, so that the first end of the sealing pin cannot be pushed forward anymore after reaching a certain limit position in the subcutaneous tissue of the subject. Besides, the stop lug boss is also used to apply a thrust imposed on the sealing pin to the indwelling tube in the process that the indwelling tube and the sealing pin enter into the subcutaneous tissue, in order to help the distal end of the indwelling tube enter into the subject. Preferably, in the fourth embodiment, the stop lug boss has a counter bore which is used in combination with an implant to push the sealing pin to enter into the subcutaneous tissue via the opening and indwelling tube.

The counter bore can be used for making the indwelling tube together with the sealing pin enter into the subcutaneous tissue of the subject more easily. When the indwelling tube and the sealing pin are needed to be pushed into the subject, one end of a rod-like implant separated from the skin surface indwelling device is placed in the counter bore, and a thrust is applied to the sealing pin and the indwelling tube by the rod-like implant to push the indwelling pin and the sealing pin into the subject.

Further, in the fourth embodiment, the skin surface indwelling device according to the present invention further comprises an adhesive element used for attaching the support onto the skin surface; wherein the adhesive element has a hole in the central section, so that the ridge portion can be exposed outside when the adhesive element covers the support.

Based on the skin surface indwelling device for guiding punctures in the fourth embodiment above, the invention also provides a method of use of the device, comprising:

(1) at the beginning of the first session, inserting the needle into the subject to carry out the first session;

(2) after the first session, removing the needle from the subject, then gradually inserting the indwelling tube together with the sealing pin into the subject through the skin surface along a puncture path of the needle until the bottom surface of the support and the skin surface are in contact with each other; and then indwelling the skin surface indwelling device on the skin surface so as to indwell the distal end of the indwelling tube and the sealing pin in the subject to hold a place, thereby helping to form a puncture tunnel;

(3) before the subsequent session, removing the sealing pin from the indwelling tube, and then inserting the needle into the subject through the tunnel of the indwelling tube to carry out the subsequent session;

(4) after the subsequent session, removing the skin surface indwelling device and the needle from the subject, and then inserting the distal end of the indwelling tube together with the sealing pin of a new skin surface indwelling device into the subject along the puncture tunnel to indwell the new skin surface indwelling device on the skin surface; repeating Steps (3) and (4) until the whole treatment is finished.

The treatment or sessions can be hemodialysis treatment or other treatments such as subcutaneous injections.

In addition, at the end of each session, the skin surface indwelling device indwelt on the skin surface can be covered with a bacteria-preventing waterproof air-permeable membrane. And before the subsequent session, the bacteria-preventing waterproof air-permeable membrane should be removed first, and then the puncture needle is punctured into the subject through the tunnel in the indwelling tube after the sealing pin is pulled out from the indwelling tube.

It can be known from the above description that the skin surface indwelling device for guiding the punctures in the fourth embodiment is disposable, which means that it is better not to be reused for the reasons that the first end of the sealing pin contacts the subcutaneous tissue of the subject in indwelling state and the sealing pin will be pulled out of the indwelling tube during the subsequent process, which results in that the sealing pin is easily polluted by environmental contaminants. Therefore, it is recommended to use a new skin surface indwelling device for each session, in order to keep the device sterile.

It should be known that the present invention are not limited to the above four embodiments. The technical features described in the present invention can be combined into various technical solutions, provided no contradiction or conflict will be result in. For example, the technical features described in the first embodiment can also be used in the second, third and fourth embodiments.

The skin surface indwelling device for guiding punctures according to the present invention can shorten the ripening time of the puncture tunnel of the buttonhole puncture method, and thus contributing to establish the puncture tunnel. Besides, the skin surface indwelling device for guiding punctures according to the present invention can also protect the unripe puncture tunnel during the puncture process. Meanwhile, the skin surface indwelling device for guiding punctures according to the present invention can also guide the puncture needle to enter into the subcutaneous tissue at an identical puncture point, an identical puncture angle and an identical puncture depth in the whole treatment, and thus allowing the buttonhole puncture method to be operated in an easier way, reducing the technical requirements for the operators, contributing to the wide spreading of the buttonhole puncture method, and preventing the patients suffering from punctures.

DETAILED DESCRIPTION OF THE INVENTION

The skin surface indwelling device for guiding punctures according to the present invention will be further described by the following embodiments along with the drawings. However, it is known that the embodiments and related descriptions should not be the limitation of the present invention.

Embodiment 1

Figure 1:
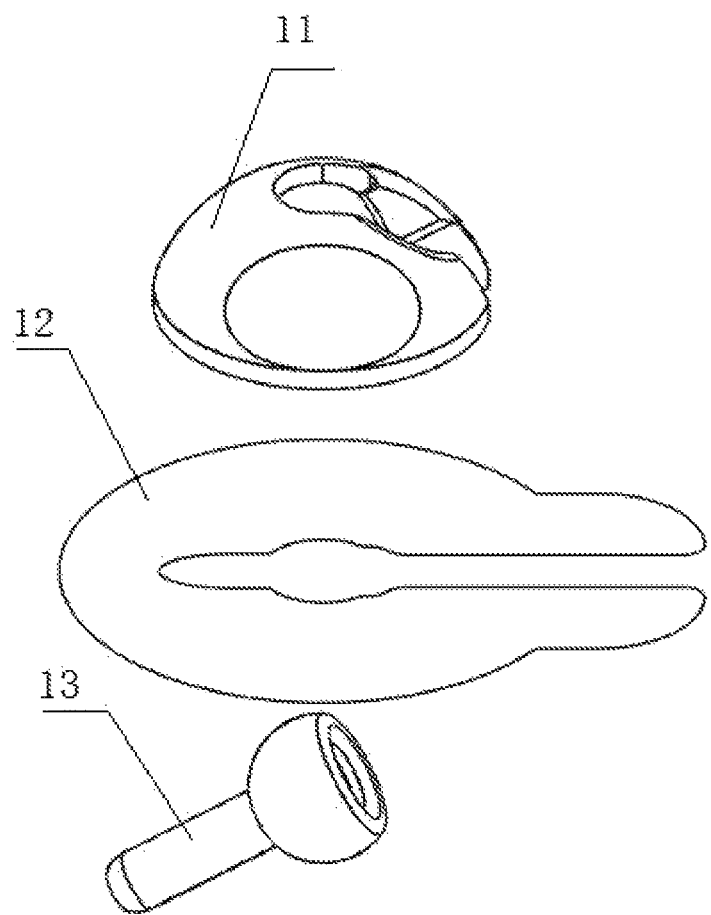
FIG. 1 shows a schematic view of the skin surface indwelling device for guiding punctures in Embodiment 1 of the present invention.

FIG. 1 shows a schematic view of the skin surface indwelling device for guiding punctures in Embodiment 1 of the present invention.

Figure 2:
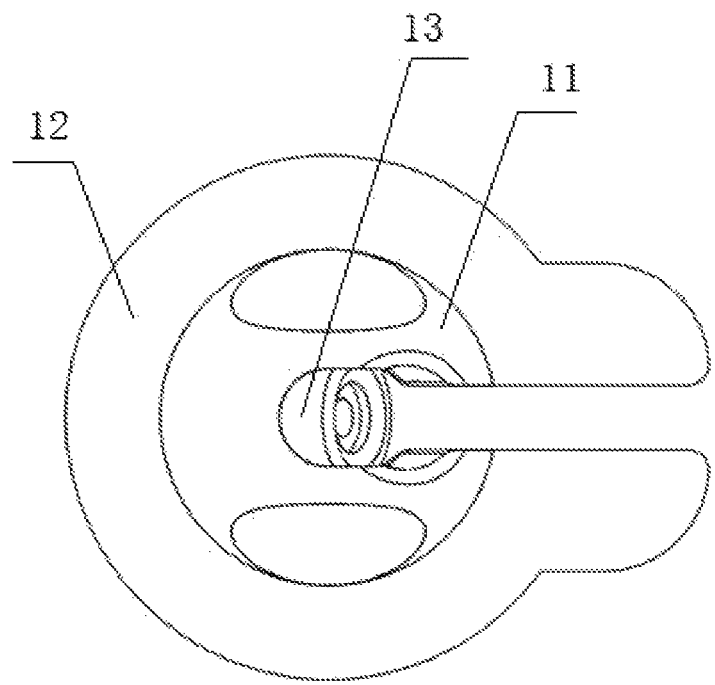
FIG. 2 shows a top view of the skin surface indwelling device for guiding punctures in Embodiment 1 of the present invention.

FIG. 2 shows a top view of the skin surface indwelling device for guiding punctures in Embodiment 1 of the present invention.

Figure 3:
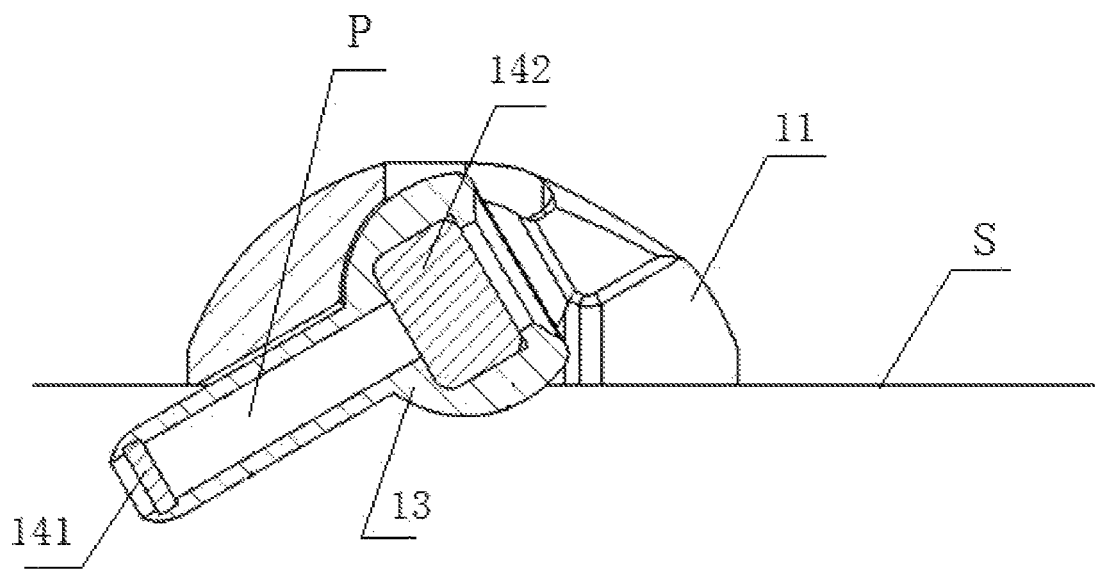
FIG. 3 shows a lateral sectional view of the skin surface indwelling device for guiding punctures in Embodiment 1 of the present invention.

FIG. 3 shows a lateral sectional view of the skin surface indwelling device for guiding punctures in Embodiment 1 of the present invention.

As shown in FIGS. 1, 2 and 3, in the embodiment, the skin surface indwelling device for guiding punctures according to the present invention comprises a support 11 made of PC, an adhesive layer 12, an indwelling tube 13 made of polyurethane, and sealing elements 141 and 142. The support 11 indirectly contacts the skin surface by the adhesive layer 12 which is adhered to the bottom surface of the support 11, providing firm support for the skin surface indwelling device. The indwelling tube 13 is connected with the support 11. The indwelling tube 13 has an inside tunnel P substantially extending along the longitudinal direction of the indwelling tube 13, and the tunnel P is used for guiding a puncture needle (not shown in the figures). In the embodiment, the diameter of the tunnel P is slightly larger than the outer diameter of the needle, in order to reduce the friction force on the needle during the process of passing through the tunnel in the indwelling tube. It can be seen from FIG. 3 that the indwelling tube 13 has a proximal end positioned above the skin surface S and a distal end positioned under the skin surface S in indwelling and occupying status. In the embodiment, the extension length of the distal end of the indwelling tube 13 is set in such a way that the bottom of the distal end is close to the vascular wall to be punctured but not in contact with the vascular wall to be punctured, in order to prevent the indwelling tube 13 from generating a pressure on the vascular wall in indwelling and occupying status. The sealing elements 141 and 142 for sealing the tunnel P are disposed in the tunnel P.

Figure 4:
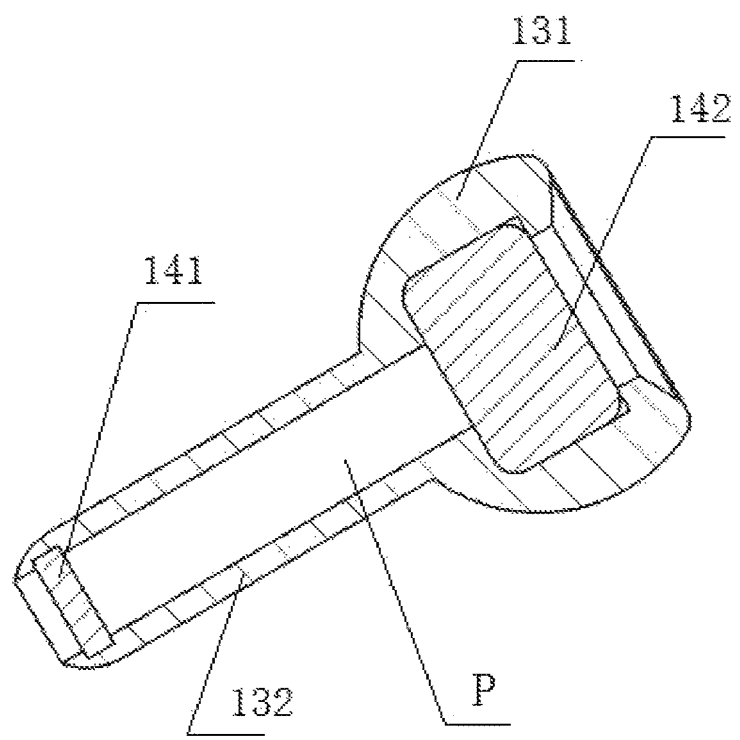
FIG. 4 shows a kind of indwelling tube of the skin surface indwelling device for guiding punctures in Embodiment 1 of the present invention.

FIG. 4 shows a kind of indwelling tube in Embodiment 1 of the present invention.

As shown in FIG. 4, the indwelling tube comprises a cylindrical tube body 132 and a spherical head 131 radially protruding from the tube body 132. The spherical head 131 can be suitably received in a spherical cavity of the support 13, so that the angle at which the indwelling tube enters into the subject is variable. In addition, a first sealing element 141 positioned to be corresponding to the distal end of the indwelling tube and a second sealing element 142 positioned to be corresponding to the proximal end of the indwelling tube are disposed in the tunnel P of the indwelling tube. The first sealing element 141 can prevent the blood or body fluid of the subject from entering into the tunnel P of the indwelling tube. The second sealing element 142 can prevent environmental contaminants from entering into the tunnel P of the indwelling tube. Alternatively, it is possible to dispose one sealing element in other embodiments. The first sealing element 141 and the second sealing element 142 are preferably configured to be seal-sealing elements which can achieve self-sealing after being punctured, and thus being reused, other than being replaced after each puncture session. The self-sealing elements can be made of silica gel, butyl rubber or other self-sealing materials. In this embodiment, the first sealing element 141 is a thin self-sealing membrane, and the second sealing element 142 is a self-sealing plug which is slightly thicker than the first sealing element 141. It can be known that the first sealing element and the second sealing element can be exchanged in other embodiments. That is, the first sealing element 141 is a self-sealing plug which is slightly thicker than the second sealing element 142 while the second sealing element 142 is a thin self-sealing membrane. Alternatively, both of the first sealing element and the second sealing element can be self-sealing membranes having roughly equal thickness.

In other embodiments, the first sealing element disposed at the distal end of the indwelling tube can also be disposed at the bottom of the distal end and to be formed as a part of the indwelling tube. The first sealing element allows the needle to enter into the subcutaneous tissue via the first sealing element while does not allow body fluid to enter into the tunnel of the indwelling tube from the subcutaneous tissue via the first sealing element. As an example, FIGS. 5 and 6 respectively show two kinds of structures of above-mentioned sealing elements.

Figure 5:
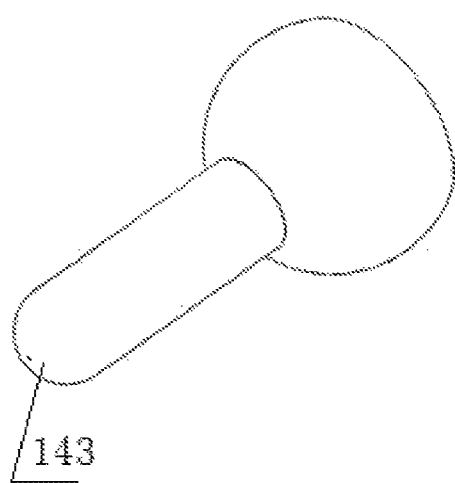
FIG. 5 shows a kind of indwelling tube with a nipple-shaped valve.

FIG. 5 shows a kind of indwelling tube with a nipple-shaped valve 143. As shown in FIG. 5, the nipple-shaped valve 143 has a hole at the end thereof, and the hole can be round-shaped, Y-shaped, cross-shaped, star-shaped or other similar structures. During operation processes, the needle can enter into the subcutaneous tissue via the hole, while the body fluid or blood of the subject cannot enter into the tunnel of the indwelling tube from the subcutaneous tissue via the hole.

Figure 6:
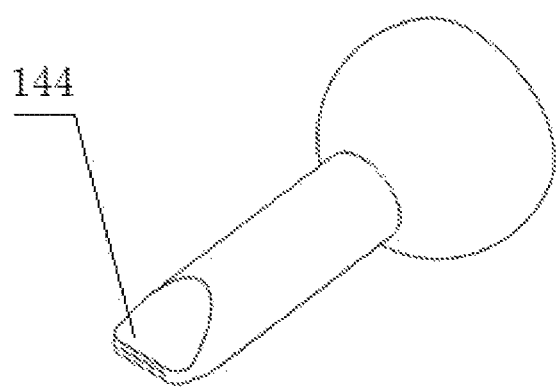
FIG. 6 shows a kind of indwelling tube with a duckbill valve.

FIG. 6 shows a kind of indwelling tube with a duckbill valve 144. As shown in FIG. 6, the duckbill valve 144 has a similar structure as duckbill and has a line-shaped opening at the end thereof. During operation processes, the needle can enter into the subcutaneous tissue via the line-shaped opening, while the body fluid or blood of the subject cannot enter into the tunnel in the indwelling tube from the subcutaneous tissue via the line-shaped opening.

Figure 7:
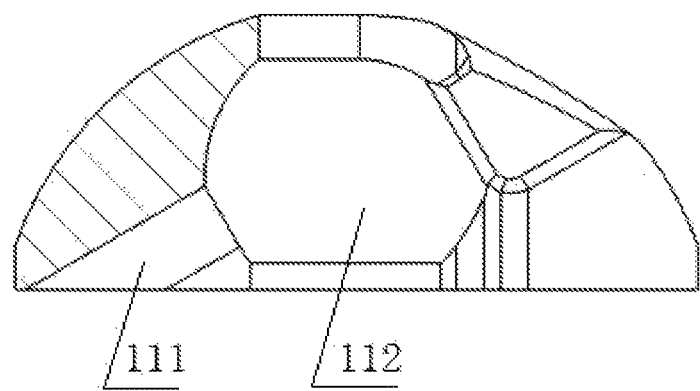
FIG. 7 shows a lateral sectional view of the support of the skin surface indwelling device for guiding punctures in Embodiment 1 of the present invention.

FIG. 7 shows a lateral sectional view of the support of the skin surface indwelling device for guiding punctures in Embodiment 1 of the present invention.

As shown in FIG. 7, the support 11 has a first cavity 111 which suitably receives the tube body 132 as shown in FIG. 4 and a second cavity 112 which suitably receives the spherical head 131 as shown in FIG. 4.

Figure 8:
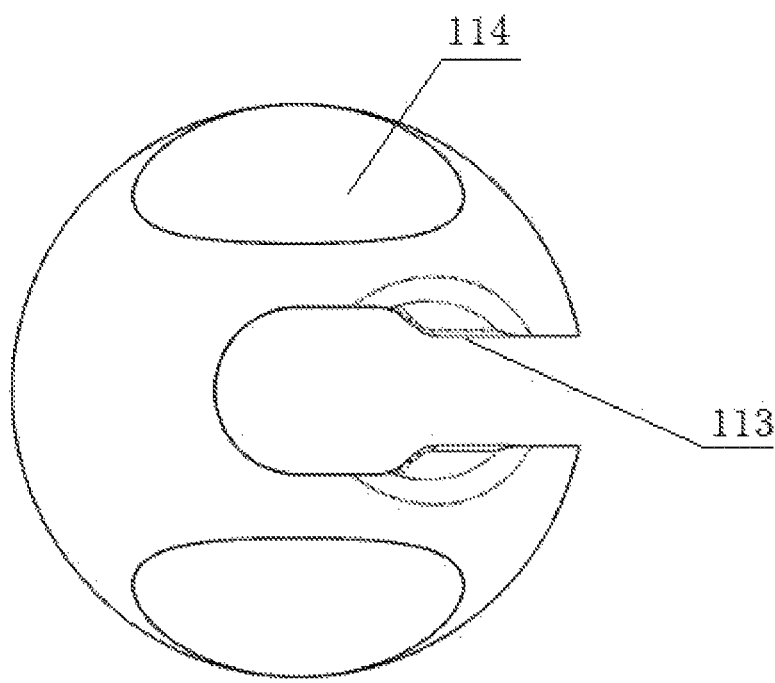
FIG. 8 shows a top view of the support as shown in FIG. 7.

FIG. 8 shows a top view of the support as shown in FIG. 7. As shown in FIG. 8, in this embodiment, the support 11 further has a U-shaped opening 113 allowing the spherical head 131 of the indwelling tube to enter into the second cavity 112. The U-shaped opening 113 is elastic and has an opening diameter which is a slightly smaller than the outer diameter of the spherical head 131. When the distal end of the indwelling tube enters the subject at a determined puncture angle, the spherical head 131 slides into the second cavity 112 of the support 11 by a force applied on the support 11, and thus the proximal end of the indwelling tube 13 is quickly connected with the support 11. In addition, it can be seen from FIG. 8 that the support 11 also has recesses 114 used for being held with fingers in this embodiment.

In this embodiment, the spherical head 131 and the second cavity 112 are connected under interference fit, in order to ensure that the spherical head 131 would not rotate relative to the second cavity 112 when the support 11 is fastened onto the indwelling tube 13.

It should be known that other configurations also can be employed to ensure that the spherical head would not rotate relative to the second cavity when the support is connected with the indwelling tube.

Figure 9:
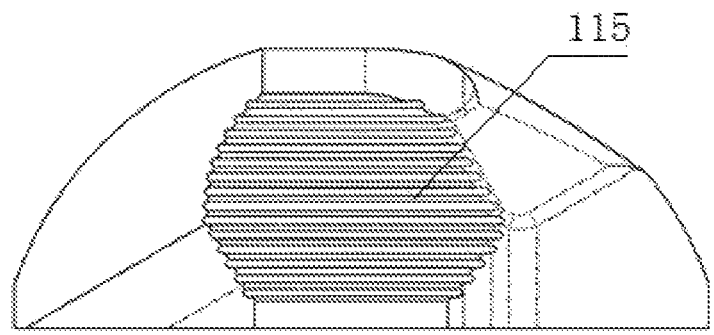
FIG. 9 shows the support in another embodiment of the present invention.

As an example, FIG. 9 shows the support in another embodiment. It can be seen from FIG. 9 that the support in this embodiment is roughly the same as that in embodiment 1, except that the inner surface of the second cavity of the support in this embodiment has raised patterns 115 which can increase the friction force between the second cavity and the spherical head of the indwelling tube, thus ensuring that the spherical head would not rotate relative to the second cavity when the support is fastened onto the indwelling tube.

Figure 10:
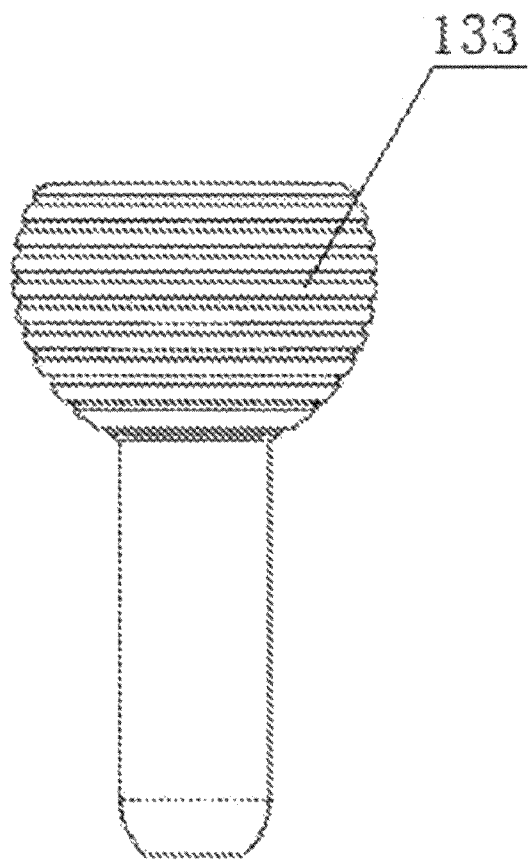
FIG. 10 shows the indwelling tube in another embodiment of the present invention.

As another example, FIG. 10 shows the indwelling tube in another embodiment. It can be seen from FIG. 10 that the indwelling tube is roughly the same as the indwelling tube in embodiment 1, except that the outer surface of the spherical head of the indwelling tube in this embodiment has raised patterns 133 which can increase the friction force between the second cavity and the spherical head of the indwelling tube, thus ensuring that the spherical head would not rotate relative to the second cavity when the support is fastened onto the indwelling tube.

In another embodiment, the inner surface of the second cavity of the support and the outer surface of the spherical head of the indwelling tube can both have raised patterns. The above mentioned raised patterns can be spiral patterns, teeth-shaped patterns or other raised patterns that can increase the friction force.

In Embodiment 1, the support 11 and the indwelling tube 13 are detachably connected. By the means of the indwelling tube as shown in FIG. 4 and the support as shown in FIG. 7, during the operation processes, the indwelling tube 13 can enter into the subject at a certain puncture angle determined by a certain operators' habits or the patients' demands. After the distal end of the indwelling tube 13 enters into the subject, the support 11 is connected with the proximal end of the indwelling tube 13, so that the angle between the bottom surface of the support 11 and the axis of the indwelling tube 13 will be unchanged. The advantages of such configuration are that the angle between the axis of the indwelling tube 13 and the bottom surface of the support 11 is variable or can be adjusted, so the skin surface indwelling devices with the same specification or standard can be suitable for different operators and patients. Generally, the angle between the bottom surface of the support 11 and the axis of the indwelling tube 13 can be varied within a range of 20-40 degrees.

The bottom surface of the support is not directly shown in the figures of the present invention. However, the bottom surface of the support 11 in Embodiment 1 preferably has a plurality of protrusions protruding from the bottom surface. On one hand, the protrusions are helpful for fixing the support, and on the other hand they can keep a certain clearance between the bottom surface and the skin surface, thus improving the air permeability of the skin surface and reducing the risk of allergy of the skin surface. The protrusions can be pyramid-shaped or hemisphere-shaped.

Figure 11:
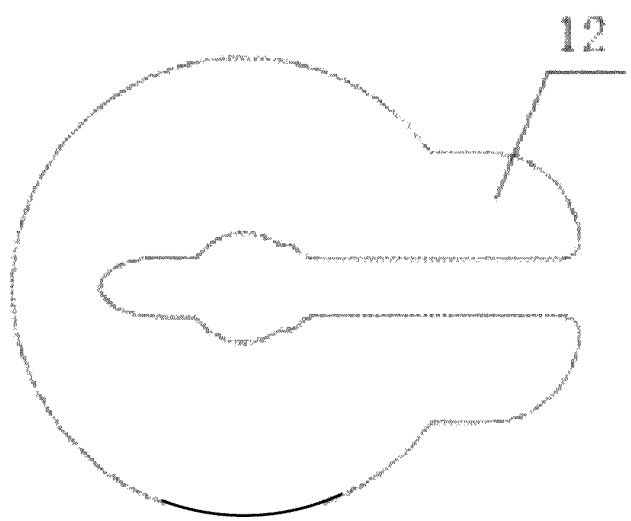
FIG. 11 shows the adhesive layer of the support of the skin surface indwelling device for guiding punctures in Embodiment 1 of the present invention.

In Embodiment 1, the support 11 is fixed onto the skin surface of the subject by the adhesive layer 12. FIG. 11 shows the adhesive layer 12 adopted in Embodiment 1. It can be seen from FIG. 11 that the adhesive layer 12 is a U-shaped adhesive layer.

Figure 12:
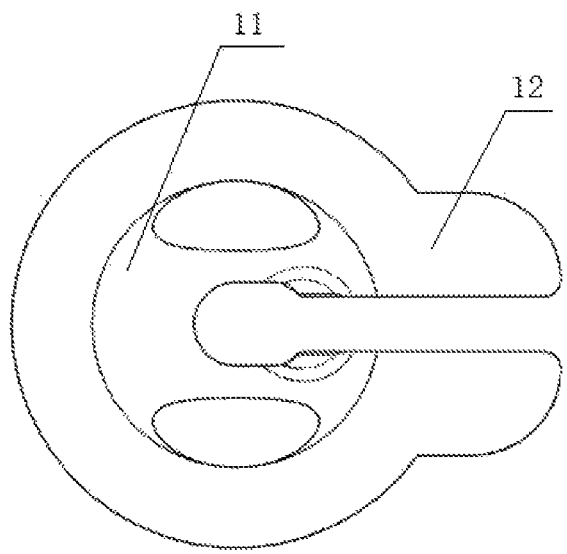
FIG. 12 shows the support is fixed onto the adhesive layer in Embodiment 1 of the present invention.

FIG. 12 shows the status that the support 11 is fixed onto the skin surface by the adhesive layer 12. As shown in FIG. 12, the bottom surface of the support 11 is adhered to the upper surface of the adhesive layer 12, and the lower surface of the adhesive layer 12 is adhered to the skin surface of the subject.

Figure 13:
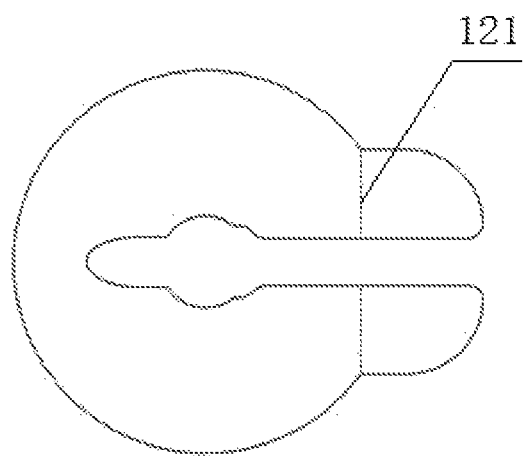
FIG. 13 shows the adhesive layer of the present invention in another embodiment.

FIG. 13 shows the adhesive layer in another embodiment. As shown in FIG. 13, the adhesive layer is a U-shaped adhesive sticker with a piece of release paper having a shear mark 121. When the support needs to be fixed, lifting up any end of the U-shaped release paper and then removing the release paper from the adhesive layer clockwise or anti-clockwise.

In addition, in this embodiment, the inner surface and/or outer surface of the indwelling tube are coated with an antibacterial coating to reduce the risk of infection during subcutaneous implantations. In other embodiments, it is possible that only the inner surface and/or outer surface of the distal end of the indwelling tube are coated with the antibacterial coating for the purpose of saving materials. The antibacterial coating can be silver ion coating, sulfadiazine coating or other antibacterial coatings known by those skilled in the art.

Preferably, the skin surface indwelling device can be covered with a layer of bacteria-preventing waterproof air-permeable membrane when it is indwelt on the skin surface of the subject, in order to further improve the antibacterial or bacteria-preventing effects. Besides, the bacteria-preventing waterproof air-permeable membrane is also helpful for fixing the skin surface indwelling device.

It can be seen from FIGS. 3, 4 and 10 that the distal end of the indwelling tube has a wedge-shaped portion with an outer diameter tapering toward the bottom of the distal end. In addition, it can be seen from FIG. 5 that the distal end of the indwelling tube has a arc-shaped portion with an outer diameter tapering toward the bottom of the distal end. Such structures can reduce the resistance to the indwelling tube during the process of entering into the subject, which makes the indwelling tube enter the subject more easily.

In the present invention, the wall thickness of the indwelling tube can be 0.1-1 mm, for example, 0.4 mm.

Figure 14:
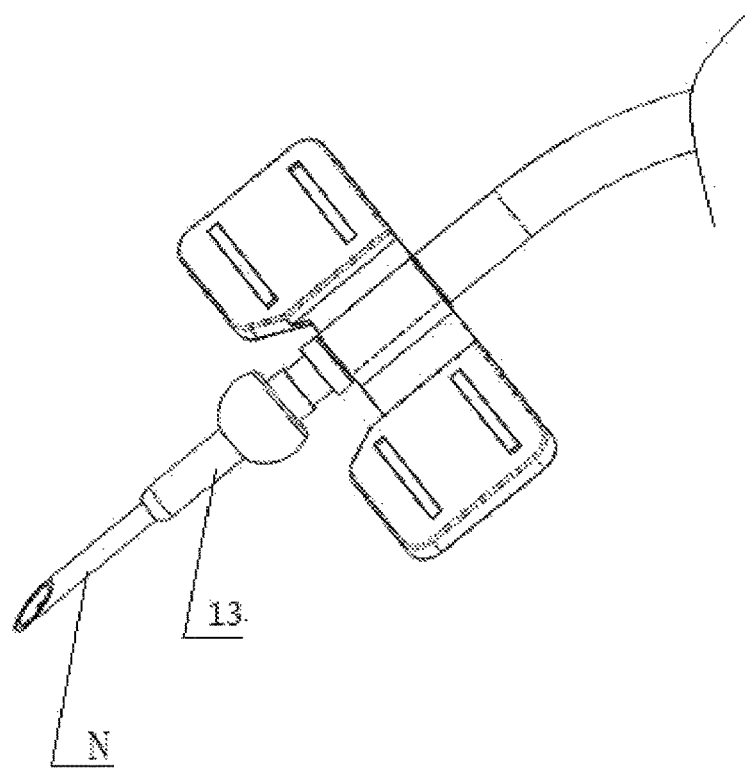
FIGS. 14, 15, 16 and 17 respectively show steps of the operating process of the skin surface indwelling device for guiding punctures in Embodiment 1 of the present invention.
Figure 15:
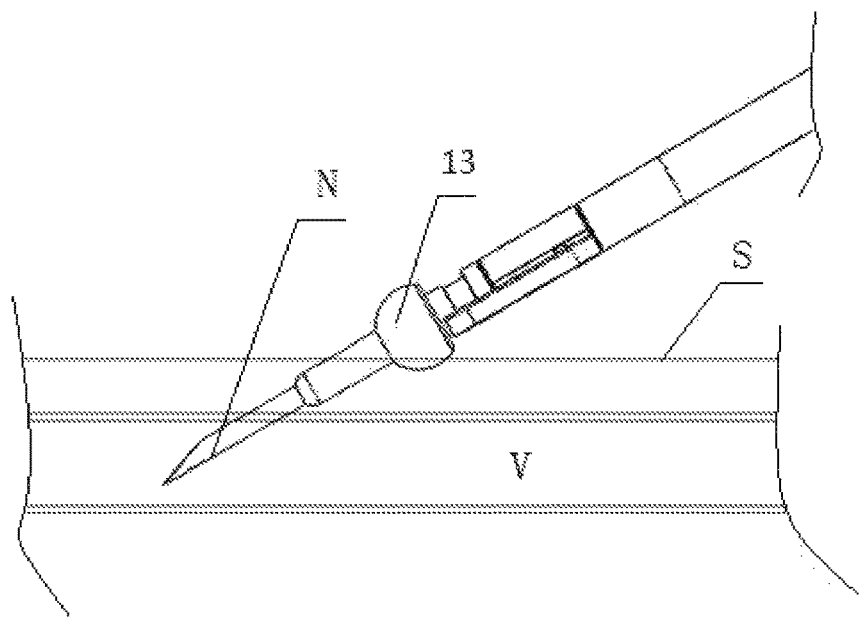
Figure 16:
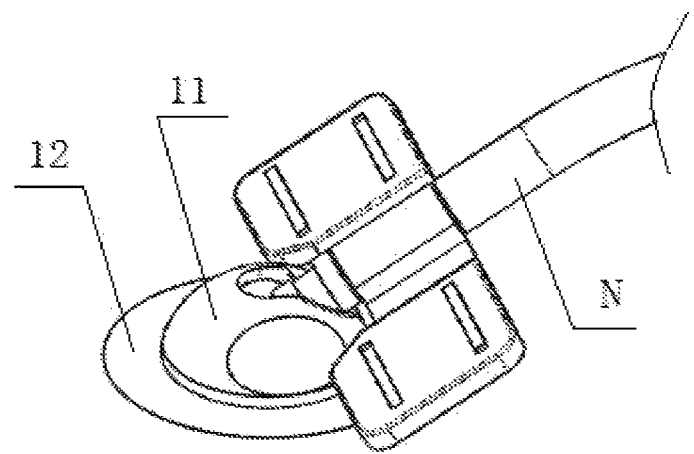

A method of use of this kind of skin surface indwelling device for guiding punctures can comprise the following steps:

(1) At the beginning of the first session, the puncture needle N passes through the tunnel of the indwelling tube 13. As shown in FIG. 14, the indwelling tube 13 is set on the puncture needle at this status. Then, the puncture needle N together with the indwelling tube 13 penetrates into the subject through the skin surface S, as shown in FIG. 15. It can be seen from FIG. 15 that the puncture needle has penetrated into the blood vessel V in this status, while the distal end of the indwelling tube 13 is under the skin surface S, the proximal end of the indwelling tube 11 is above the skin surface S and the bottom of the distal end is close to the vascular wall V but not in contact with the vascular wall V. And then, as shown in FIG. 16, the support 11 is connected to the proximal end of the indwelling tube 13, and the support 13 is fixed onto the skin surface by the adhesive layer 12, so that the angle between the bottom surface of the support 11 and the axis of the indwelling tube 13 is kept unchanged. The first session is carried out in such status.

Figure 17:
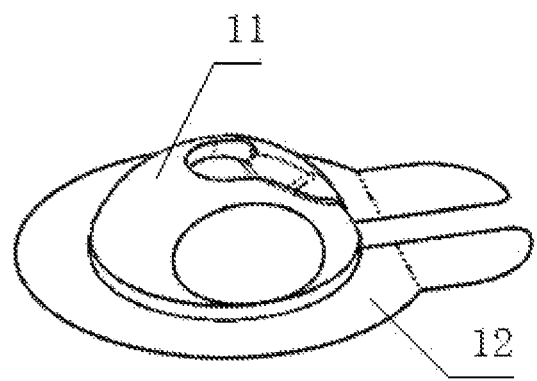

(2) When the first session is finished, the puncture needle is pulled out of the subject, while the skin surface indwelling device is indwelt on the skin surface due to the limit from the support 11, as shown in FIG. 17. The distal end of the indwelling tube is indwelt in the subject for occupying and thus forming the puncture tunnel. In such status, the first sealing element in the tunnel can prevent the blood or body fluid of the subject from entering into the indwelling tube, and the second sealing element in the tunnel can prevent environmental contaminants from entering into the indwelling tube. Then, the skin surface indwelling device is covered with a layer of bacteria-preventing waterproof air-permeable membrane. After that, the patient can go home with the skin surface indwelling device.

(3) Before the subsequent session begins, the bacteria-preventing waterproof air-permeable membrane is removed first, and then a conventional sterilization is carried out. Then, the puncture needle passes through the tunnel in the indwelling tube and enters into the subject to carry out the subsequent session.

Step (3) is repeated until the whole treatment is finished.

It should be understood that the indwelling tube in Step (3) can be an old indwelling tube of an old skin surface indwelling device indwelt on the skin surface used in the last session, or a new indwelling tube of a new skin surface indwelling device replacing for the old skin surface indwelling device used in the last session. That is, the skin surface indwelling device in Embodiment 1 can be reused in several sessions, and it is not necessary to replace a new one for each session. The skin surface indwelling device in Embodiment 1 can be indwelt on the skin surface for 3-5 days, or be reused for 3-5 sessions. It should be known that the indwelling time or the applying time of one skin surface indwelling device can be properly increased or reduced according to the biocompatibility of the skin surface indwelling device.

Besides, it should be understood that the puncture needle used in the first session can be a sharp needle which is the same as those used in other sessions or a blunt needle. Adopting the blunt needle is more helpful for creating a wider puncture tunnel.

Embodiment 2

Figure 18:
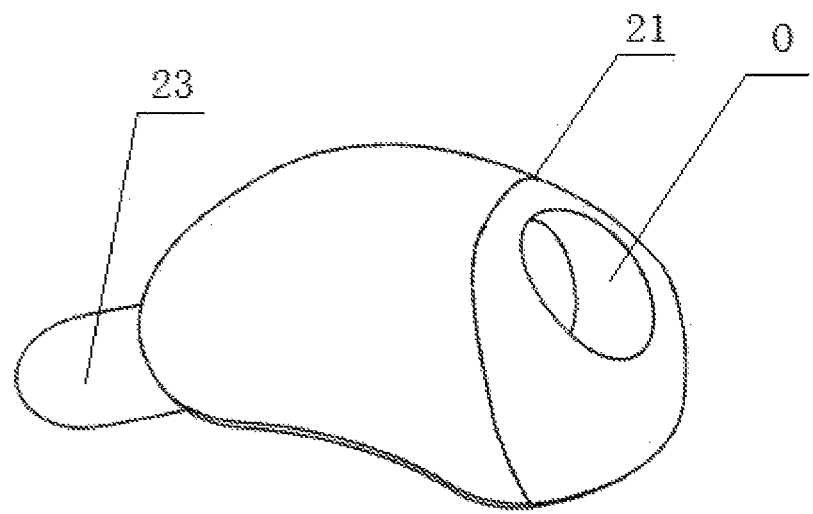
FIG. 18 shows a schematic view of the skin surface indwelling device for guiding punctures in Embodiment 2 of the present invention.
Figure 19:
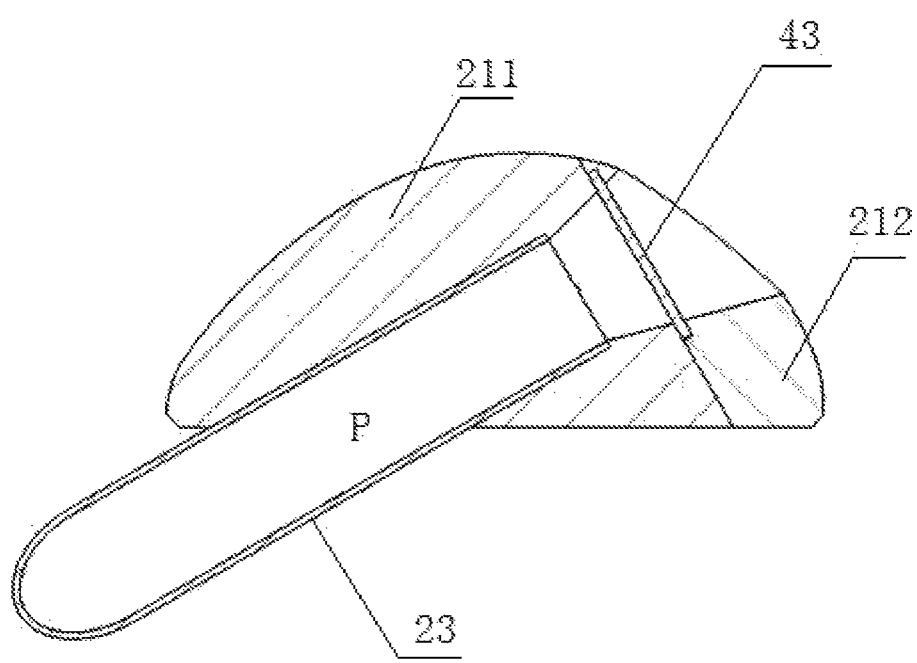
FIG. 19 shows a lateral sectional view of the skin surface indwelling device for guiding punctures as shown in FIG. 18.

FIGS. 18 and 19 show the structure of the skin surface indwelling device for guiding punctures in Embodiment 2 of the present invention.

As shown in FIGS. 18 and 19, in this embodiment, the skin surface indwelling device for guiding punctures comprises a mouse-shaped support 21 made of PC, an indwelling tube fixedly connected with the support 21. The support 21 comprises a supporting portion 211 and a cover 212 separated with the supporting portion 211. The support 21 has an opening O and a cavity which is communicated with the opening O and is used for accommodating the indwelling tube. It can be seen from FIG. 19 that the opening O is wedge-shaped with an inwardly decreasing diameter, which can guide for the puncture needle entering into the tunnel. The bottom surface of the support 21 contacts the skin surface of the subject under indwelling state. In this embodiment, the indwelling tube is configured as a blind tube 23 with the bottom of the distal end closed and the proximal end opened. The blind tube 23 has an inside tunnel P substantially extending along the longitudinal direction thereof. The tunnel P is used for guiding a puncture needle (not shown in the figures). In the embodiment, the diameter of the tunnel P is slightly larger than the outer diameter of the needle, in order to reduce the friction force on the needle during the process of passing through the tunnel. A part of the blind tube 23 that is positioned above the skin surface is a proximal end, and the other part positioned under the skin surface is a distal end. The extension length of the distal end of the blind tube 23 is set in such a way that the bottom of the distal end is close to the vascular wall to be punctured but not in contact with the vascular wall to be punctured, in order to avoid that pressure is applied on the vascular under indwelling state. In this embodiment, the closed bottom of the blind tube 23 is formed as a part of the sealing element of the present invention, and the closed bottom can be penetrated by the puncture needle. In addition, the closed bottom in this embodiment is arc-shaped, in order to reduce the resistance to the blind tube when the blind tube enters into the subject. Besides, the sealing elements in this embodiment further comprise a sealing membrane 43 disposed between the supporting portion 211 and the cover 212. The sealing membrane can prevent environmental contaminants from entering into the blind tube 23. The sealing membrane 43 can be made of silica gel, PTEE, or other macromolecular materials that meet requirements.

In this embodiment, the blind tube 23 is fixedly but not detachably connected to the support 21. Such fixed connection can be implemented via bond or other methods known by those skilled in the art. In such configuration, the angle between the axis of the blind tube 23 and the bottom surface of the support 21 in one skin surface indwelling device is unchanged and cannot be adjusted. Therefore, the skin surface indwelling devices can be produced with various specifications or standards for meeting various requirements from different operators and patients, so that the angles between bottom surfaces of the supports and the axis of the blind tubes of the skin surface indwelling devices with various specifications can be various in a certain range, such as a range from 20 degrees to 40 degrees. Besides, the lengths of the distal ends of the indwelling tubes of the skin surface indwelling devices with various specifications can be various.

In this embodiment, the wall thickness and/or hardness of the closed bottom of the distal end of the blind tube 23 is preferably smaller than those of the other parts of the of the blind tube 23 for the reasons that the wall thickness and/or hardness of the closed bottom should be smaller for the purpose of punctures, while the wall thickness and/or hardness of the other parts of the of the blind tube should be higher for ensuring enough strength, so that to provide a sufficient support force during the process of occupying and forming the puncture tunnel and to provide a better protection for the tissues of the subject during the process of the puncture needle penetrating into the subject.

In this embodiment, the inner surface and/or outer surface of the blind tube 23 are preferably coated with an anti-bacterial coating, in order to reduce the risk of infections during subcutaneous implantations. In other embodiments, it is possible that only the inner surface and/or outer surface of the distal end of the blind tube 23 are coated with the anti-bacterial coating. The anti-bacterial coating can be silver ion coating, sulfadiazine coating or other anti-bacterial coatings known by those skilled in the art.

The bottom surface of the support 21 preferably has a plurality of protrusions protruding from the bottom surface, although they are not directly shown in FIGS. 18 and 19. On one hand, the protrusions are helpful for fixing the support, and on the other hand they can keep a certain clearance between the bottom surface and the skin surface, thus improving the air permeability of the skin surface and reducing the risk of allergy of the skin surface.

Preferably, the skin surface indwelling device in the embodiment can be covered with a layer of bacteria-preventing waterproof air-permeable membrane, so that to further improve antibacterial or bacteria-preventing effects.

Besides, the bacteria-preventing waterproof air-permeable membrane is also helpful for fixing the skin surface indwelling device.

In addition, the support 21 in this embodiment can have recesses used for being held with fingers, although they are not shown in FIG. 18.

A method of use of this kind of skin surface indwelling device for guiding punctures can comprise the following steps:

(1) At the beginning of the first session, a puncture needle is pierced into a subject to perform the first session.

(2) When the first session is finished, the puncture needle is pulled out of the subject, and then the distal end of the blind tube is pierced into the subject through the skin surface along the puncture path of the puncture needle until the surface bottom of the support contacts with the skin surface. After that, the skin surface indwelling device is indwelt on the skin surface and the distal end of the blind tube is indwelt in the subject for occupying, used for forming the puncture tunnel. Then, the skin surface indwelling device is covered with a bacteria-preventing waterproof air-permeable membrane, and then the patient can go home with the skin surface indwelling device.

Figure 20:
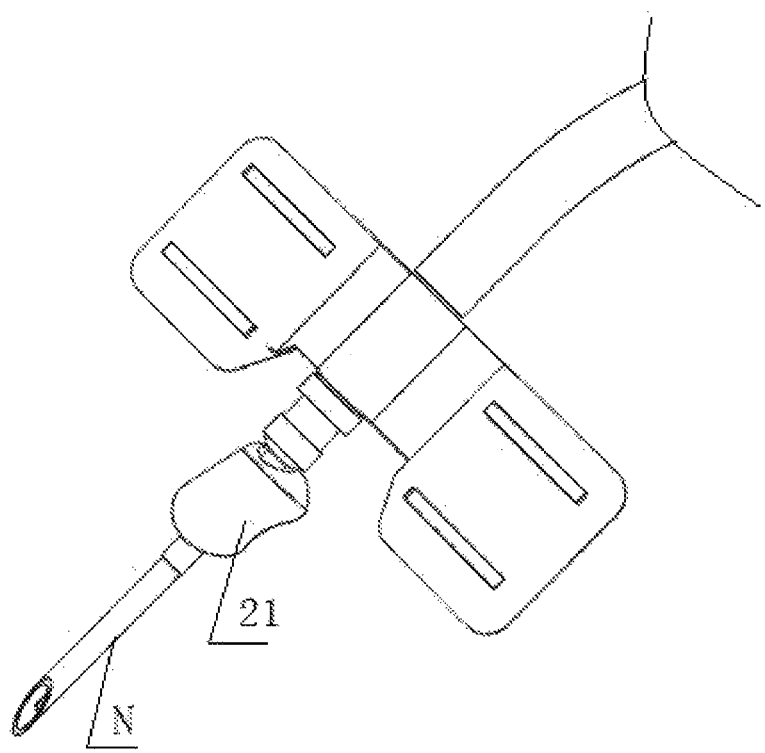
FIG. 20 shows the status in use of the skin surface indwelling device for guiding punctures in Embodiment 2 of the present invention.

(3) Before the subsequent session begins, the bacteria-preventing waterproof air-permeable membrane is removed, and a conventional sterilization is carried out. And then, the puncture needle N passes through the tunnel in the blind tube to enter into the subject to perform the subsequent session, as shown in FIG. 20 (The skin surface, tissues and blood vessels of the subject are not shown in the figure).

(4) When the subsequent session is finished, the skin surface indwelling device and the puncture needle are pulled out of the subject, and then the distal end of the blind tube of a new skin surface indwelling device is immediately punctured into the subject along the puncture tunnel, so that the new skin surface indwelling device is indwelt on the skin surface.

Step (3) and Step (4) are repeated until the whole treatment is finished.

The treatment can be hemodialysis treatment or other treatments, for example subcutaneous injections.

It can be known from the above description that such skin surface indwelling device for guiding punctures is disposal, which means that the skin surface indwelling device does not allow being reused. Once the bottom of the blind tube is punctured, a new skin surface indwelling device is needed to replace the old one after the session, in order to ensure the sealing effect. However, it also should be known that the skin surface indwelling device can be reused if the blind tube has a self-sealing element.

Embodiment 3

Figure 21:
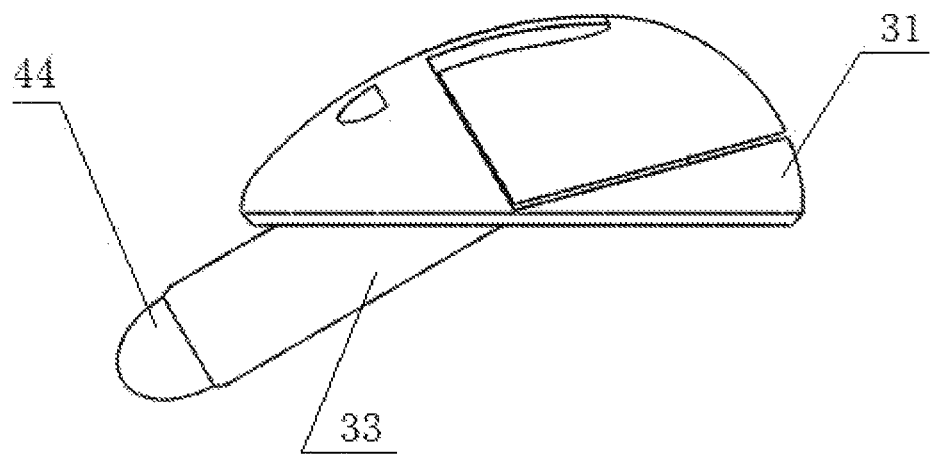
FIG. 21 shows a lateral view of the skin surface indwelling device for guiding punctures in Embodiment 3 of the present invention.

FIG. 21 shows a lateral view of the skin surface indwelling device for guiding punctures in Embodiment 3 of the present invention.

Figure 22:
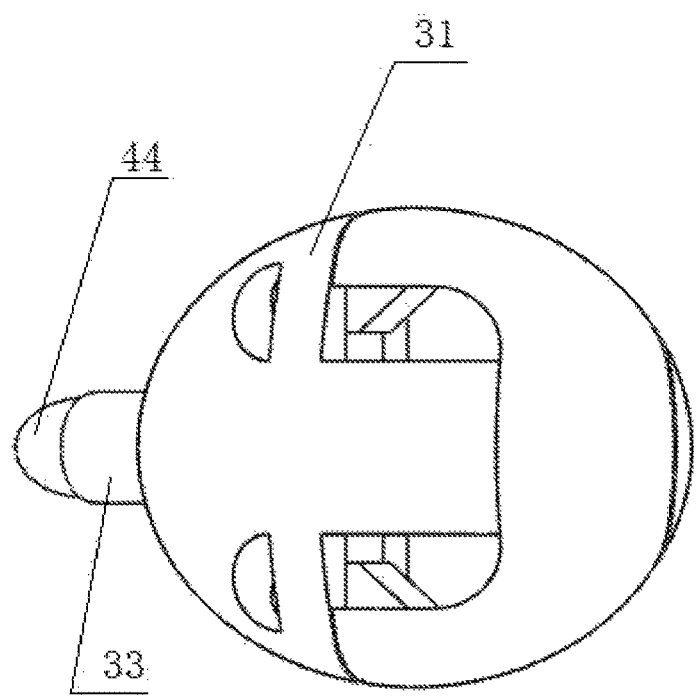
FIG. 22 shows a top view of the skin surface indwelling device for guiding punctures in Embodiment 3 of the present invention.

FIG. 22 shows a top view of the skin surface indwelling device for guiding punctures in Embodiment 3 of the present invention.

Figure 23:
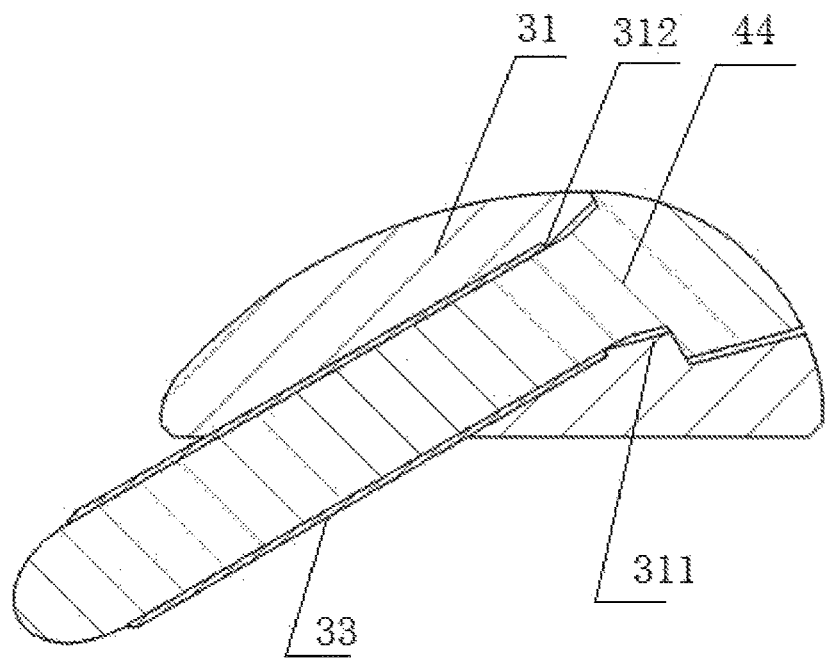
FIG. 23 shows a lateral sectional view of the skin surface indwelling device for guiding punctures in Embodiment 3 of the present invention.

FIG. 23 shows a lateral sectional view of the skin surface indwelling device for guiding punctures in Embodiment 3 of the present invention.

As shown in FIGS. 21, 22 and 23, in this embodiment, the skin surface indwelling device for guiding punctures comprises a support 31 made of PC, an indwelling tube 33 fixedly disposed in the support 31 and a sealing pin 44. The support has an opening 311. The sealing pin 44 is inserted into the indwelling tube 33 via the opening 311. A first end (i.e. a bottom end) of the sealing pin 44 extends out of the bottom of the distal end of the indwelling tube 33. It can be seen from FIG. 23 that the opening 311 is wedge shaped with an inwardly decreasing diameter, in order to provide a guidance for puncture needle (not shown in the figure) entering into the tunnel.

Figure 24:
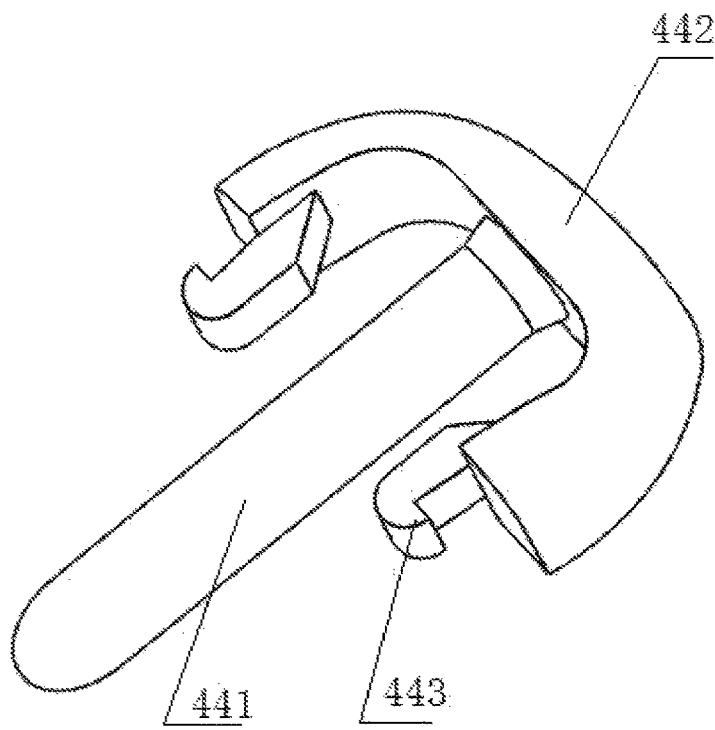
FIG. 24 shows the sealing pin of the skin surface indwelling device for guiding punctures in Embodiment 3 of the present invention.

The sealing element in this embodiment is a sealing pin 44 different from those in Embodiment 1 and Embodiment 2. FIG. 24 shows the structure of the sealing pin in this embodiment. As shown in FIG. 24, the sealing pin 44 comprises a pin body 441 and a connecting element which is connected with the pin body 441. The pin body 441 is coaxially disposed in the indwelling tube 33, and the first end of the pin body 441 extends out of the bottom of the distal end of the indwelling tube 33. Thus, when the skin surface indwelling device is indwelt on the skin surface, the part of the pin body which extends out of the bottom of the distal end of the indwelling tube 33 is also used for occupying. Besides, the other part of the pin body disposed in the indwelling tube 33 can be used for enhancing the strength of the wall of the indwelling tube. In addition, in this embodiment, the first end of the pin body 441 is set in such a way that the first end is close to the vascular wall to be punctured but not in contact with the vascular wall to be punctured, in order not to increase the pressure applied on the vascular wall. Because the first end of the pin body 441 extends out of the bottom of the distal end of the indwelling tube 33, it should be known that the bottom of the distal end of the indwelling tube 33 is also close to the vascular wall to be punctured but not in contact with the vascular wall to be punctured, and the first end of the pin body 441 is closer to the vascular wall relative to the bottom of the distal end of the indwelling tube. Moreover, it can be seen from FIG. 24 that the first end of the pin body 441 in this embodiment is arc-shaped for the purpose of reducing the resistance when the pin body together with the indwelling tube enters into the subject. In this embodiment, the connecting element is configured to be a structure which can be quickly connected and disconnected to the support. Specifically, the connecting element comprises a U-shaped beam 442 which is fixedly connected with a second end of the pin body 441, and first claws 443 which are respectively disposed at the ends of two arms of the U-shaped beam 442.

Figure 25:
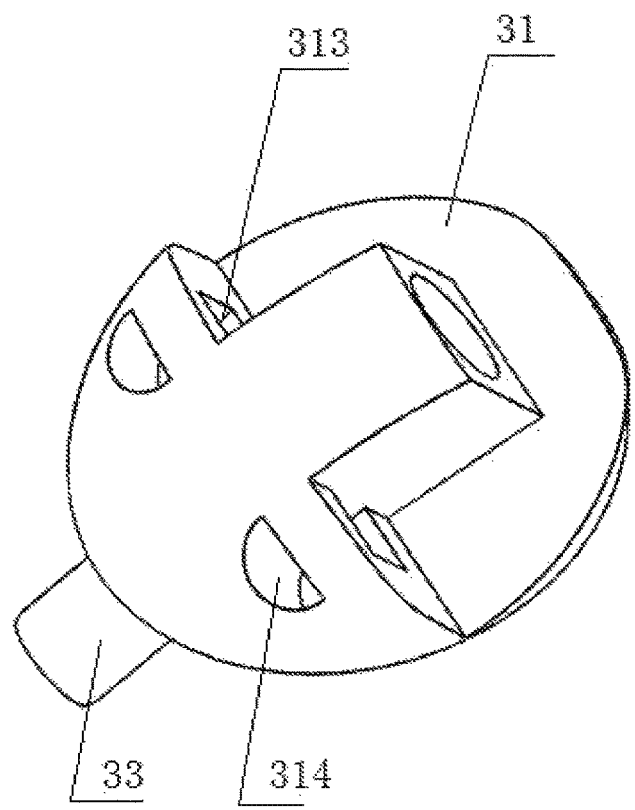
FIG. 25 shows the support and the indwelling tube of the skin surface indwelling device for guiding punctures in Embodiment 3 of the present invention.

FIG. 25 shows the structures of the support and the indwelling tube of the skin surface indwelling device for guiding punctures in Embodiment 3 of the present invention. It can be seen from FIG. 25 that the support 31 has a cavity inside for accommodating the indwelling tube 33, and the indwelling tube 33 is disposed in the cavity. It can be seen from FIG. 23 that the cavity has a lug boss 312 inwardly protruded from the inner surface of the cavity. The lug boss 312 is used for preventing the indwelling tube 33 from going on being pushed forward after the indwelling tube 33 reaches a certain location inside the cavity. Thus, the indwelling tube 33 can be positioned quickly relative to the support 31. It can be seen from FIG. 25 that the support 33 has two matching grooves 313 respectively matched with the first claws 443, in order to make the support 31 be quickly connected and disconnected with the sealing pin 44.

When the sealing pin 44 is needed to be connected to the support 31, the two arms of the U-shaped beam 442 are pressed toward each other to drive the pair of first claws 443 to get close to each other, and then the first claws 443 are inserted into the matching grooves 313 respectively. After that, the pressure is released, thus the two arms of the U-shaped beam 442 together with the two first claws 443 is recovered under the elastic force. In this status, the first claws 443 are disposed in the matching grooves 313, and thus the sealing pin 44 has been connected with the support 31. When the sealing pin 44 is needed to be removed from the support 31, the two arms of the U-shaped beam 442 are pressed toward each other again to drive the pair of the first claws 443 to get close to each other, and then the first claws 443 are pulled out of the matching grooves 313, and thus the sealing pin 44 are disconnected to the support 31. It can also be seen from FIG. 25 that the support 31 further has process holes 314 for forming the matching grooves 313 by injection molding.

It can also be seen from FIGS. 23 and 24 that the pin body 441 in this embodiment is equal in diameter in the axial direction and the pin body 441 is consistently in close fit with the indwelling tube 33 in the axial direction. A better sealing effect can be achieved by means of the pin body 441 being consistently in a close fit with the indwelling tube 33. Besides, the pin body 441 is consistently in a close fit with the indwelling tube 33, thus the pin 441 can provide a bigger support force to the wall of the indwelling tube 33.

Figure 26:
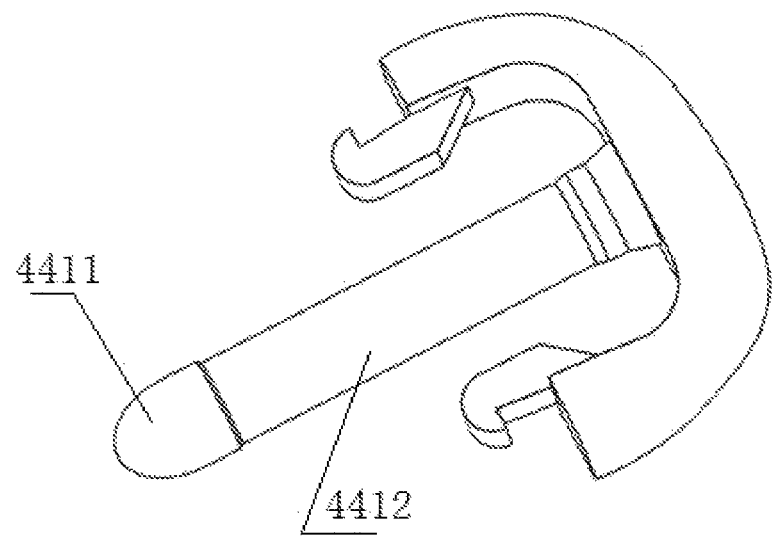
FIG. 26 shows a kind of sealing pin in another embodiment of the present invention.
Figure 27:
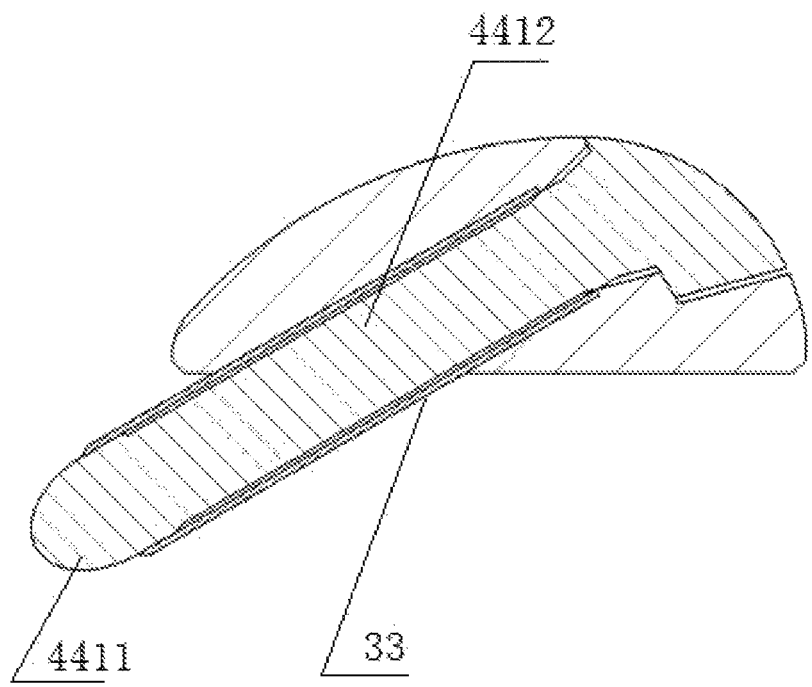
FIG. 27 shows the status that the pin of the sealing pin as shown in FIG. 26 is disposed in the indwelling tube.

FIGS. 26 and 27 show another kind of sealing pin disposed in the indwelling tube in another embodiment of the present invention. The sealing pin as shown in FIGS. 26 and 27 is different from the sealing pin as shown in FIGS. 23 and 24 in that the pin body of the sealing pin as shown in FIGS. 26 and 27 is not equal in diameter in the axial direction, but comprises at least two portions which are different in outer diameter. The outer diameter of a distal portion 4411 is slightly larger than that of a body portion 4412. It can be seen from FIG. 27 that the distal portion 4411 of the pin body is in close fit with the indwelling tube 33 to ensure the sealing effect, so that the blood or body fluid of the subject cannot enter into the indwelling tube; while the outer diameter of the body portion 4412 of the pin body is slightly smaller than the inner diameter of the indwelling tube 33 to generate a certain clearance between the body portion 4412 of the pin body and the indwelling tube 33. Such structure can reduce the friction force applied on the pin body when the pin body gets in and out of the indwelling tube, and make the process of pin body getting in and out of the indwelling tube more easily relative to the structure as shown in FIGS. 23 and 24.

Figure 28:
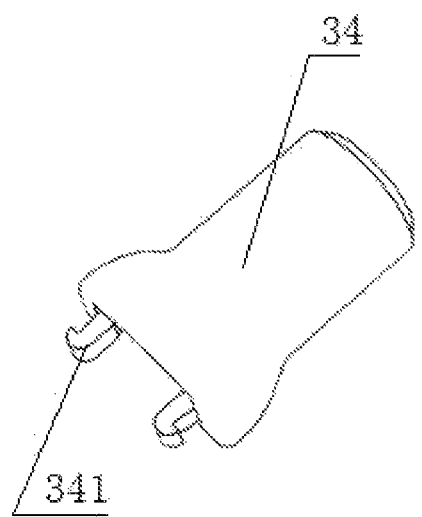
FIG. 28 shows an auxiliary element which is preferably provided in the skin surface indwelling device for guiding punctures in Embodiment 3 of the present invention.
Figure 29:
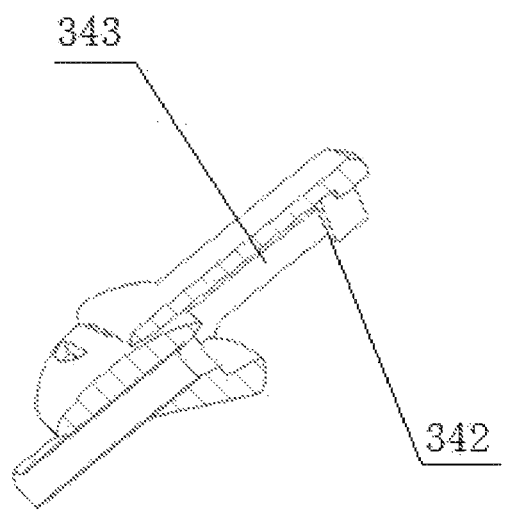
FIG. 29 shows a sectional view of the auxiliary element as shown in FIG. 28.

Preferably, the device can also comprise an auxiliary element in order to remove the skin surface-indwelling device easily. The auxiliary element can be connected with the support as shown in FIGS. 21-23, 25, and can also be connected with the support as shown in FIG. 27. FIG. 28 schematically shows the structure of the auxiliary element. And FIG. 29 shows a sectional view of the auxiliary element. As shown in FIGS. 28 and 29, a first end of the auxiliary element 34 is provided with second claws 341 which respectively match with the matching grooves 313 on the support 31. The processes of the second claws 341 being connected and disconnected to the matching grooves 313 are similar to the processes of the first claws 443 being connected and disconnected to the matching grooves 313 as mentioned above. A second end of the auxiliary element 34 has a connecting portion for being connected with the puncture needle, for example, a radially inward lug boss 342 as shown in FIG. 29. The lug boss 342 is used for matching with a corresponding groove on the puncture needle, thus achieving the connection between the puncture needle and the auxiliary element. It is also possible to configure the connecting portion in other ways, such as threaded connection, fastening connection, pin connection, etc. It can also be seen from FIG. 29 that the auxiliary element 34 further has a groove 343 for accommodating the puncture needle.

Figure 30:
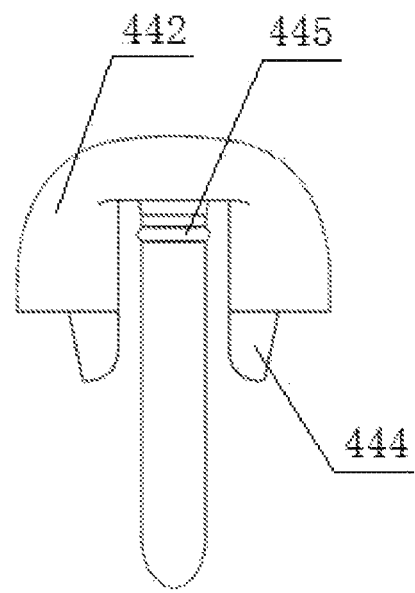
FIG. 30 shows the sealing pin in a further embodiment of the present invention.
Figure 31:
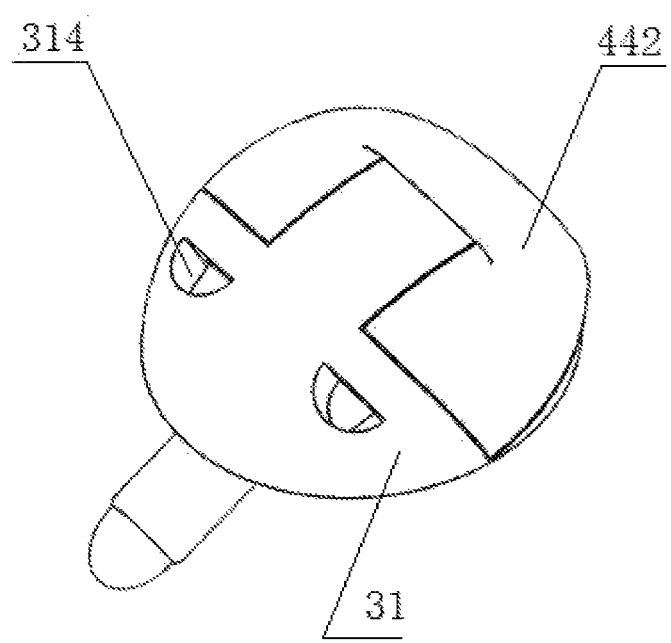
FIG. 31 shows the connection between the sealing pin as shown in FIG. 30 and the support.

FIGS. 30 and 31 show another embodiment of the quick connection and disconnection between the connecting element of the sealing pin and the support. It can be seen from FIG. 30 that the connecting element fixedly connected to the second end of the pin body also comprises a U-shaped beam 442. The ends of the two arms of the U-shaped beam 442 are provided with wedged guideposts 444. The second end of the pin body is further provided with an O-shaped ring 445. The support as shown in FIG. 31 has matching holes (not shown in the figure) which match with the wedged guide posts 444. Besides, the support 31 is also provided with process holes 314 for forming the matching holes by injection molding. When the sealing pin is inserted into the indwelling tube to seal the indwelling tube, the wedged guide posts 444 are correspondingly inserted into the matching holes of the support 31. Thus the sealing pin can be steadily connected with the support by the enhanced friction force between the pin body and the support brought from the O-shaped ring 445 disposed between the pin body and the support. When the sealing pin is needed to be pulled out of the indwelling tube, a pulling force which is greater than the friction force should be applied to the sealing pin.

It should be known that the pin body as shown in FIG. 30 is equal in diameter in the axial direction thereof, however the pin body can also be configure to have the same structure as that shown in FIG. 26.

In Embodiment 3, the pin body can be solid or hollow. The solid pin body can provide a stronger support force for the wall of the indwelling tube relative to a hollow pin body; while the hollow pin body saves more materials and has a lighter weight.

Preferably, in Embodiment 3, the outer surface of the pin body and the inner and/or outer surfaces of the indwelling tube are coated with antibacterial coatings. The anti-bacterial coatings can be sliver ion coating, sulfadiazine coating or other antibacterial coatings known by those skilled in the art.

In addition, although it is not shown in the figures of this embodiment, the bottom surface of the support 31 is preferably has a plurality of protrusions which protrude out of the bottom surface. On one hand, the protrusions provided on the bottom surface can improve, the fixing effect; and on the other hand, the protrusions provided on the bottom surface can form a certain clearance between the bottom surface and the skin surface, thus improving the air permeability of the skin surface and reducing the risk of allergy of the skin surface.

Preferably, the skin surface indwelling device in this embodiment can also be covered with a bacteria-preventing waterproof air-permeable membrane, thus further improving the anti-bacterial and bacteria-preventing effects. Besides, the bacteria-preventing waterproof air-permeable membrane is also helpful for fixing the skin surface indwelling device.

In addition, in another embodiment, the support can also have recesses for being held with fingers.

Besides, the inner diameter of the indwelling tube 33 in this embodiment is preferably slightly larger than the outer diameter of the puncture needle.

In this embodiment, the angle between the bottom surface of the support 31 and the axis of the indwelling tube 33 of the skin surface indwelling device can be set in a range of 20 degrees to 40 degrees. However, it should be known that, for one skin surface indwelling device, the angle between the bottom surface of the support 31 and the axis of the indwelling tube 33 cannot be changed or adjusted.

Under the condition that the sealing pin is connected to the support, the outer profile of the support in this embodiment can be hemisphere-shaped, arch-shaped or mouse-shaped in order to be conveniently held by the operators.

A method of use of this kind of skin surface indwelling device for guiding punctures can comprise the following steps:

(1) At the beginning of the first session, a puncture needle is first punctured into a subject to perform the first session.

(2) When the first session is finished, the puncture needle is pulled out of the subject, then the distal end of the indwelling tube together with the sealing pin are gradually punctured into the subject through the skin surface along the puncture path of the puncture needle until the bottom surface of the support contact the skin surface. The skin surface indwelling device is indwelt on the skin surface and the distal end of the indwelling tube together with the sealing pin are indwelt in the subject for occupying, thus helping for forming the puncture tunnel. And then the skin surface indwelling device is covered with a bacteria-preventing waterproof air-permeable membrane. After that, the patient can go home with the skin surface indwelling device.

Figure 32:
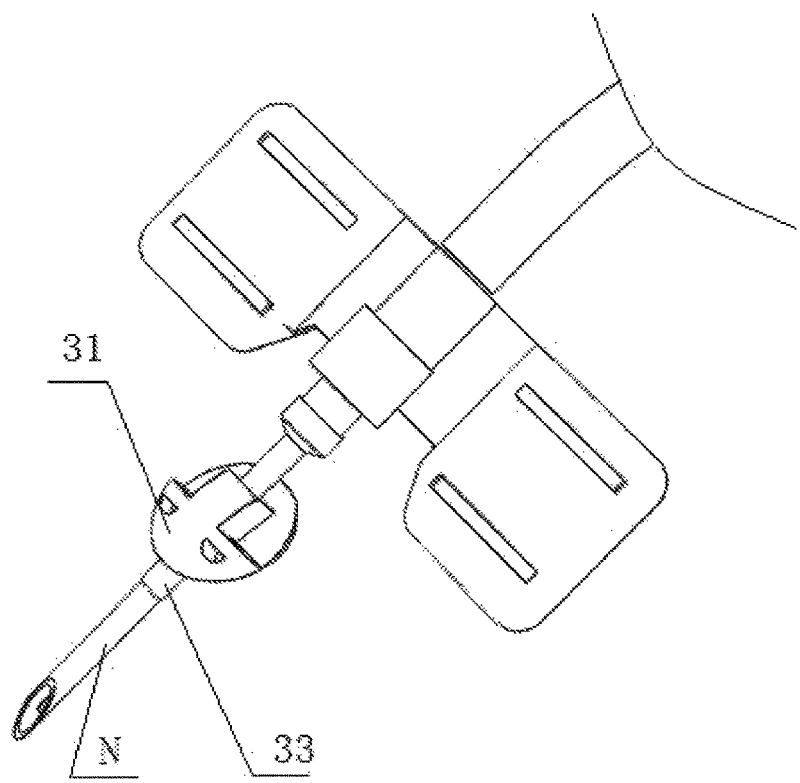
FIG. 32 and FIG. 33 respectively show the different status in use of the skin surface indwelling device for guiding punctures in Embodiment 3 of the present invention.

(3) Before the subsequent session begins, the bacteria-preventing waterproof air-permeable membrane is removed and the sealing pin is pulled out of the indwelling tube. And then the puncture needle N passes through the tunnel in the indwelling tube and enters into the subject to perform the subsequent session, as shown in FIG. 32.

(4) When the subsequent session is finished, the skin surface indwelling device and the puncture needle are pulled out of the subject. And then the distal end of the indwelling tube together with the sealing pin of a new skin surface indwelling device are immediately punctured into the subject along the puncture tunnel, so that the new skin surface indwelling device is indwelt on the skin surface.

Step (3) and Step (4) are repeated until the whole treatment is finished.

The treatment or sessions can be hemodialysis treatment or other treatments, such as subcutaneous injections.

It can be known from the above description that such skin surface indwelling device is also disposable, which means that it cannot be reused for the reasons that the bottom end of the pin body of the sealing pin contacts the subcutaneous tissue of the subject in the indwelling status and the sealing pin will be pulled out of the indwelling tube in the subsequent process, resulting in that the sealing pin is easily polluted by environmental contaminants. Therefore, it is recommended to use a new skin surface indwelling device for each session in order to keep the device sterile.

Figure 33:
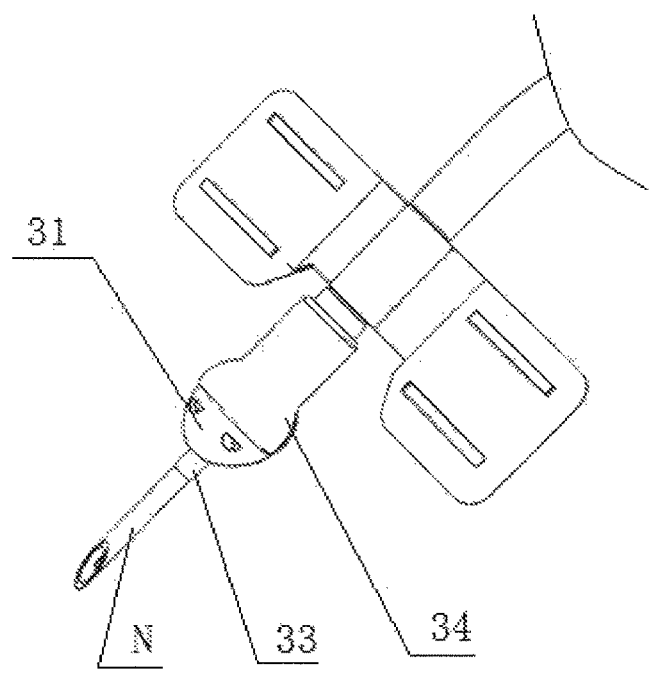

When the skin surface indwelling device comprises the above mentioned auxiliary element, Step (3) further comprises the following procedures: Before the subsequent session begins, the sealing pin is pulled out of the indwelling tube. And then the puncture needle N which is connected with the auxiliary element 34 passes through the tunnel in the indwelling tube 33 and enters into the subject until the puncture needle reaches at a subcutaneous position. And then the auxiliary element 34 is connected to the support 31, as shown in FIG. 33. After that, the subsequent session can be carried out. And Step (4) further comprises the following procedures: When the subsequent session is finished, the skin surface indwelling device and the puncture needle N are pulled out of the subject by a force applied on the puncture needle N. And then the distal end of the indwelling tube together with the sealing pin of a new skin surface indwelling device are immediately punctured into the subject along the puncture tunnel, so that the new skin surface indwelling device is indwelt on the skin surface.

Embodiment 4

Figure 34:
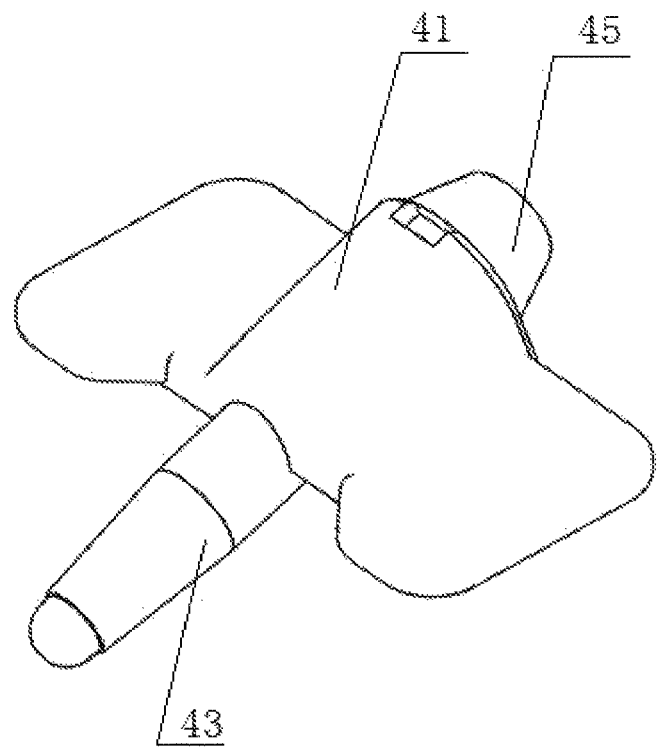
FIG. 34 shows a schematic view of the skin surface indwelling device for guiding punctures in Embodiment 4 of the present invention.

FIG. 34 shows a schematic view of the skin surface indwelling device for guiding punctures in Embodiment 4 of the present invention.

Figure 35:
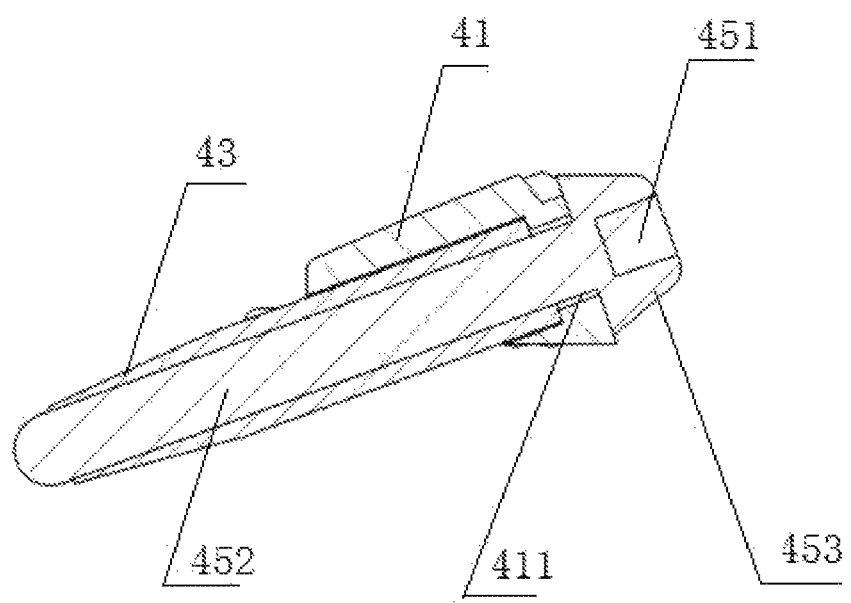
FIG. 35 shows a lateral sectional view of the skin surface indwelling device as shown in FIG. 34.

FIG. 35 shows a lateral sectional view of the skin surface indwelling device as shown in FIG. 34.

As shown in FIGS. 34 and 35, in this embodiment, the skin surface indwelling device for guiding punctures comprises a support 41 made of silica gel, an indwelling tube 43 disposed in the support 41 and a sealing pin 45. The support has an opening 411. The sealing pin 45 is inserted into the indwelling tube 43 via the opening 411, and has a first end which extends out of the bottom of the distal end of the indwelling tube 43. The first end of the sealing pin extends out of the bottom of the distal end of the indwelling tube, so the first end of the sealing pin can also be used for occupying in indwelling state. Besides, the part of sealing pin which is disposed in the indwelling tube can help for enhancing the strength of the wall of the indwelling tube. In addition, in this embodiment, the first end of the sealing pin 45 is set in such a way that the first end is close to the vascular wall to be punctured but not in contact with the vascular wall to be punctured, in order not to increase the pressure applied on the vascular wall. Because the first end of the sealing pin 45 extends out of the bottom of the distal end of the indwelling tube 43, it should be known that the bottom of the distal end of the indwelling tube 43 is also close to the vascular wall to be punctured but not in contact with the vascular wall to be punctured, and the first end of the sealing pin 45 is closer to the vascular wall relative to the bottom of the distal end of the indwelling tube 43. In this embodiment, the sealing pin 45 comprises a pin body 452 and a stop lug boss 453 connected with a second end of the pin body 452. The stop lug boss 453 prevents the pin body 452 from further extending out of the indwelling tube in the axial direction of the indwelling tube, thus the first end of the pin body cannot be pushed forward anymore after reaching a certain limit position in the subcutaneous tissue of the subject. Besides, the stop lug boss 453 also further applies the thrust imposed on the sealing pin to the indwelling tube in the process that the indwelling tube and the sealing pin enter into the subcutaneous tissue to assist the distal end of the indwelling tube to enter into the subject. It can also be seen from the figure that the first end of the pin body 452 is arc-shaped for the purpose of reducing the resistance to the pin body and the indwelling tube during the process of entering into the subject. It can also be seen from FIG. 35 that the pin body 452 in this embodiment is equal in diameter in the axial direction thereof and the pin body 452 is consistently in close fit with the indwelling tube 43 in the axial direction, resulting in a better sealing effect. In addition, the pin body 452 can provide a stronger support force for the tube wall of the indwelling tube 43 because the pin body 452 is consistently in close fit with the indwelling tube 43.

Figure 36:
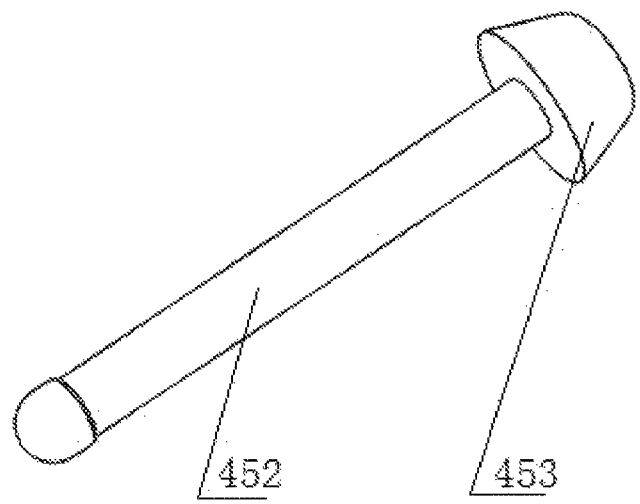
FIG. 36 shows another kind of sealing pin in another embodiment, which is different from the structure of the sealing pin in Embodiment 4.

FIG. 36 shows the sealing pin in another embodiment. The sealing pin also has a pin body 452 and a stop lug boss 453 connected with the second end of the pin body 452. However, the pin body of the sealing pin as shown in FIG. 36 is different from the sealing pin as shown in FIG. 35 in that the pin body of the sealing pin as shown in FIG. 36 is not equal in diameter in the axial direction thereof and comprises at least two portions which are different in outer diameter, wherein the outer diameter of a distal portion is larger than the outer diameter of a body portion. Therefore, when the sealing pin is inserted into the indwelling tube, the distal portion of the pin body is in close fit with the indwelling tube 43, thus ensuring the sealing effect that the blood or body fluid of the subject cannot enter into the indwelling tube. A certain clearance exists between the body portion of the pin body and the indwelling tube 43 due to the outer diameter of the body portion of the pin body is slightly smaller than the inner diameter of the indwelling tube 43, which can reduce the friction force on the sealing pin during the process of the sealing pin getting in and out of the indwelling tube, and thus making the sealing pin get in and out of the indwelling tube more easily relative to the structure as shown in FIG. 35.

Figure 37:
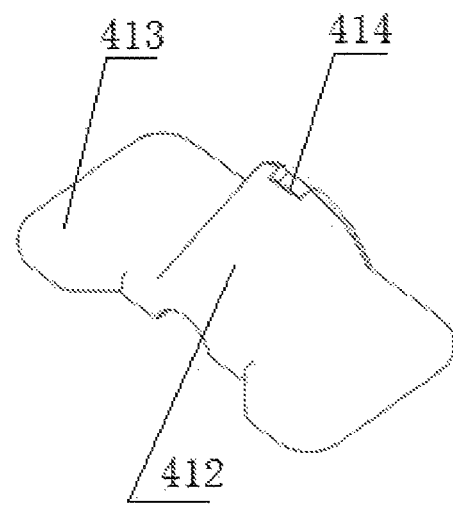
FIG. 37 shows the support of the skin surface indwelling device for guiding punctures in Embodiment 4 of the present invention.

FIG. 37 shows the support of the skin surface indwelling device for guiding punctures in Embodiment 4 of the present invention.

Figure 38:
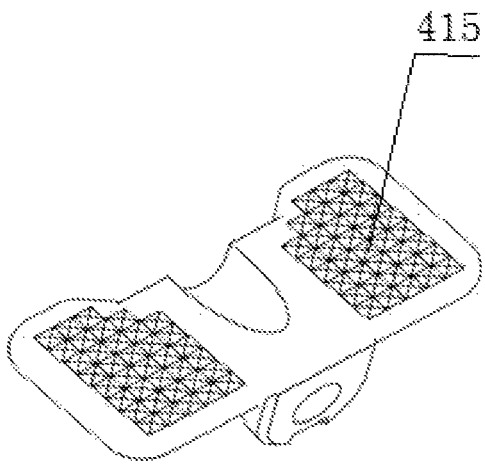
FIG. 38 shows another view of the support in Embodiment 4.

FIG. 38 shows another view of the support in Embodiment 4.

As shown in FIGS. 37 and 38, the support comprises a ridge portion 412 and wings 413 extending out from the ridge portion. The ridge portion 412 has a groove 414 served as a point where a force is applied to take the sealing pin out of the indwelling tube at its first end, thus helping for pulling the sealing pin out of the indwelling tube.

It can be seen from FIG. 38 that a plurality of pyramid-shaped protrusions 415 protruding from the bottom surface is provided on the bottom surface of the support 41. On one hand, the protrusions provided on the bottom surface can improve the fixing effect; and on the other hand, the protrusions provided on the bottom surface can form a certain clearance between the bottom surface and the skin surface, thus improving the air permeability of the skin surface and reducing the risk of allergy of the skin surface. It is possible that the protrusions can be configured to be other shapes in other embodiments, such as hemisphere-shaped.

It can also be seen from FIG. 35 that the stop lug boss 453 of the sealing pin 45 has a counter bore 451 which is used in combination with an implant. When it needs to push the indwelling tube and the sealing pin into the subject, one end of a rod-like implant independent from the skin surface indwelling device is correspondingly placed in the counter bore 451, and the indwelling tube and the sealing pin can be pushed into the subject by applying a thrust to the sealing pin and the indwelling tube via the rod-like implant.

In this embodiment, the pin body can be solid or hollow. The solid pin body can provide a stronger support force to the tube wall of the indwelling tube in view of the hollow pin body; while the hollow pin body saves more materials and has a lighter weight.

In addition, the outer surface of the pin body and the inner surface and/or outer surface of the indwelling tube are preferably coated with antibacterial coatings. The anti-bacterial coatings can be sliver ion coating or sulfadiazine coating, or other antibacterial coatings known by those skilled in the art.

Besides, the inner diameter of the indwelling tube 43 in this embodiment is preferably slighter larger than the outer diameter of the puncture needle to reduce the friction force generated by the puncture needle entering into the indwelling tube 43.

In this embodiment, the angles between the bottom surface of the support 41 and the axis of the indwelling tube 43 of the skin surface indwelling device with various specifications can be set in a range of 20 degrees to 40 degrees. However, it should be known the angle between the bottom surface of the support 41 and the axis of the indwelling tube 43 for one skin surface indwelling device cannot be changed.

Figure 39:
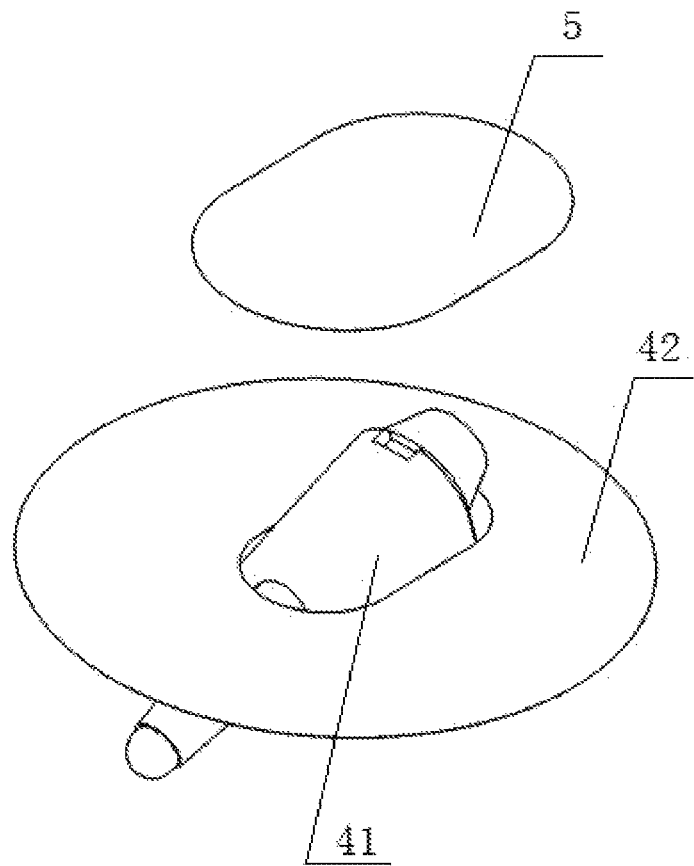
FIG. 39 shows the status that the skin surface indwelling device in Embodiment 4 is fixed onto the skin surface of a subject.

FIG. 39 shows the status that the skin surface indwelling device in Embodiment 4 is fixed onto the skin surface of a subject.

It can be seen from FIG. 39 that the skin surface indwelling device further comprises an adhesive element 42 used for attaching the support 41 onto the skin surface. The adhesive element 42 has a hole in the central area, so that the ridge portion 412 is exposed outside while the wings 413 are covered and adhered to the skin surface of the subject, when the adhesive element 42 covers the support 41. Besides, the surface indwelling device is covered with a bacteria-preventing waterproof air-permeable membrane 5 when indwelt on the skin surface, thus further improving the antibacterial and bacteria-preventing effects. Besides, the bacteria-preventing waterproof air-permeable membrane 5 can further help for fixing the skin surface indwelling device.

A method of use of this kind of skin surface indwelling device for guiding punctures can comprises the following steps:

(1) At the beginning of the first session, a puncture needle is punctured into a subject to perform the first session.

(2) After the first session is finished, the puncture needle is pulled out of the subject, then the distal end of the indwelling tube together with the sealing pin are gradually punctured into the subject through the skin surface along the puncture path of the puncture needle until the bottom surface of the support contacts the skin surface. Then the skin surface indwelling device is attached onto the skin surface by adhesive element, so that the distal end of the indwelling tube and the sealing pin are indwelt in the subject for occupying, thus used for forming the puncture tunnel. Then the skin surface indwelling device is covered with a bacteria-preventing waterproof air-permeable membrane. After that, the patient can go home with the skin surface indwelling device.

(3) Before the subsequent session begins, the bacteria-preventing waterproof air-permeable membrane is removed and the sealing pin is pulled out of the indwelling tube, and then the puncture needle passes through the tunnel in the indwelling tube to perform the subsequent session.

(4) When the subsequent session is finished, the skin surface indwelling device and the puncture needle are pulled out of the subject. And then the distal end of the indwelling tube along with the sealing pin of a new skin surface indwelling device are immediately punctured into the subject along the puncturing tunnel, so that the new skin surface indwelling device is indwelt on the skin surface.

Step (3) and Step (4) are repeated until the whole treatment is finished.

The treatment or sessions can be hemodialysis treatment or other treatments, such as subcutaneous injections.

It can be known from the above description that such skin surface indwelling device is disposable, which means that it is suitable for reused for the reasons that the first end of the sealing pin contacts the subcutaneous tissue of the subject in indwelling state and the sealing pin will be pulled out of the indwelling tube during the subsequent operation process, resulting in that the sealing pin is quite easy to be polluted by environmental contaminants. Therefore, it is recommended to use a new skin surface indwelling device for each session in order to keep the device sterile.

One skilled in the art will understand that various combinations and/or modifications and variations can be made in the described devices and methods depending upon the specific needs for operation. Moreover, features illustrated or described as being part of an aspect or embodiment of the invention may be used in the other aspects or embodiments of the invention, either alone or in combination.

The invention claimed is:

1. A skin surface indwelling device configured to guide punctures, the device comprising: an indwelling tube having an inside tunnel substantially extending along a longitudinal direction of the indwelling tube, wherein the tunnel is configured to receive a needle, and wherein the indwelling tube has a proximal end configured to be positioned above a skin surface and a distal end configured to be positioned under the skin surface in an indwelling state; a support having a bottom surface that is configured to directly or indirectly contact the skin surface, wherein the support is configured to support the indwelling tube; and sealing elements configured to seal the inside tunnel, wherein the indwelling tube is configured to connect to the support at a plurality of different angles, and wherein after the indwelling tube and the support are connected, an angle between the bottom surface of the support and an axis of the indwelling tube is fixed, wherein the indwelling tube comprises a head configured to be received in a cavity defined by the support at the plurality of different angles, wherein the head is configured to fit into the cavity by an interference fit to fix the angle between the bottom surface of the support and the axis of the indwelling tube, wherein the head does not rotate relative to the cavity upon being received in the cavity.

2. The device of claim 1, wherein an extension length of the distal end of the indwelling tube is set in such a way that a bottom of the distal end is close to a vascular wall to be punctured but not in contact with the vascular wall to be punctured.

3. The device of claim 1, further comprising the needle, wherein a diameter of the inside tunnel of the indwelling tube is slightly larger than an outer diameter of the needle.

4. The device of claim 1, wherein the plurality of different angles includes angles from 20 degrees to 40 degrees between the bottom surface of the support and the axis of the indwelling tube.

5. The device of claim 1, wherein an inner surface and/or an outer surface of the indwelling tube or an inner surface and/or an outer surface of the distal end of the indwelling tube is coated with an antibacterial coating.

6. The device of claim 1, further comprising a plurality of protrusions protruding from the bottom surface of the support.

7. The device of claim 1, further comprising a bacteria-preventing waterproof air-permeable membrane which covers a portion of the skin surface indwelling device configured to be above the skin surface when the indwelling tube is in the indwelling state.

8. The device of claim 1, wherein an outer contour of the support is hemisphere-shaped, arch-shaped or mouse-shaped.

9. The device of claim 1, wherein the support has recesses for being held with fingers.

10. The device of claim 1, wherein the support is detachably connected with the indwelling tube, the support is configured that the angle between the bottom surface of the support and the axis of the indwelling tube keeps unchanged while the support is connected with the proximal end of the indwelling tube.

11. The device of claim 1, wherein the indwelling tube comprises a tube body and the head, the head being a spherical head radially protruding from the tube body, wherein the spherical head is provided on the proximal end of the indwelling tube, and wherein the cavity comprises a first cavity configured to receive the spherical head, and the support further defines a second cavity configured to receive part of the tube body.

12. The device of claim 11, wherein an outer surface of the spherical head and/or an inner surface of the first cavity has raised patterns which increase a friction force between an outer surface of the spherical head and an inner surface of the first cavity.

13. The device of claim 11, wherein the support has a U-shaped opening configured to allow the spherical head to enter into the first cavity.

14. The device of claim 13, wherein the U-shaped opening is an elastic U-shaped opening with an opening diameter which is slightly smaller than an outer diameter of the spherical head.

15. The device of claim 1, wherein the head comprises a spherical head and the cavity comprises a spherical cavity.

16. The device of claim 15, wherein the spherical head does not rotate relative to the spherical cavity upon being received in the spherical cavity.

17. The device of claim 1, wherein the sealing elements are positioned in the inside tunnel of the indwelling tube, wherein the sealing elements comprise a first sealing element and a second sealing element proximal to the first sealing element.

18. The device of claim 1, wherein the sealing elements are self-sealing.

19. The device of claim 1, wherein the sealing elements comprise silica gel or butyl rubber.

* * * * *